(12) United States Patent
Harrison

(10) Patent No.: US 8,695,592 B2
(45) Date of Patent: Apr. 15, 2014

(54) PARTICULATE DISPENSER

(75) Inventor: Ian Harrison, Oxfordshire (GB)

(73) Assignee: Alchemy Healthcare Ltd., Oxfordshire (GB)

( * ) Notice: Subject to any disclaimer, the term of this patent is extended or adjusted under 35 U.S.C. 154(b) by 180 days.

(21) Appl. No.: 12/736,507

(22) PCT Filed: Apr. 14, 2009

(86) PCT No.: PCT/GB2009/050359
§ 371 (c)(1),
(2), (4) Date: Jan. 31, 2011

(87) PCT Pub. No.: WO2009/127860
PCT Pub. Date: Oct. 22, 2009

(65) Prior Publication Data
US 2011/0114671 A1    May 19, 2011

(30) Foreign Application Priority Data

Apr. 14, 2008 (GB) .................................. 0806735.7

(51) Int. Cl.
*A61M 15/00* (2006.01)
*A61M 16/00* (2006.01)

(52) U.S. Cl.
USPC .................................................... 128/203.21

(58) Field of Classification Search
USPC ............. 128/200.14, 200.18, 200.22, 200.23, 128/203.15, 203.19, 203.21; 222/3–6, 80, 222/81, 129, 635
See application file for complete search history.

(56) References Cited

U.S. PATENT DOCUMENTS

| | | |
|---|---|---|
| 4,599,082 A | 7/1986 | Grimard |
| 5,215,221 A | 6/1993 | Dirksing |
| 6,062,213 A * | 5/2000 | Fuisz et al. ............... 128/200.21 |
| 6,427,688 B1 | 8/2002 | Ligotke et al. |
| 2001/0027790 A1 | 10/2001 | Gieschen et al. |
| 2003/0047184 A1 | 3/2003 | Lockhart et al. |
| 2005/0028813 A1 | 2/2005 | Harrison |
| 2006/0169278 A1* | 8/2006 | Djupesland et al. ..... 128/200.14 |
| 2006/0237010 A1* | 10/2006 | De Boer et al. .......... 128/203.15 |
| 2007/0151562 A1* | 7/2007 | Jones et al. ............... 128/203.21 |
| 2007/0163574 A1* | 7/2007 | Rohrschneider et al. ......................... 128/200.19 |
| 2007/0240714 A1* | 10/2007 | Dunne et al. ............. 128/203.15 |
| 2008/0006269 A1 | 1/2008 | Lockhart et al. |
| 2009/0084380 A1* | 4/2009 | Gieschen et al. ........ 128/203.15 |
| 2011/0073106 A1* | 3/2011 | Harmer et al. ........... 128/200.23 |
| 2011/0083668 A1* | 4/2011 | Jones et al. ............... 128/203.21 |
| 2011/0277763 A1* | 11/2011 | Sullivan et al. .......... 128/203.15 |

FOREIGN PATENT DOCUMENTS

| | | |
|---|---|---|
| EP | 1 757 321 | 2/2007 |
| WO | 01/56640 | 8/2001 |
| WO | 02/056950 | 7/2002 |
| WO | 03/030973 | 4/2003 |
| WO | 2004/004922 | 1/2004 |

OTHER PUBLICATIONS

International Search Report for PCT/GB2009/050359 (European Patent Office, Kroeders, Marleen), mailed Aug. 17, 2009.

* cited by examiner

*Primary Examiner* — Kristen Matter
(74) *Attorney, Agent, or Firm* — Nixon & Vanderhye P.C.

(57) ABSTRACT

The present invention provides for elements of an improved drug or medicine dispersion and delivery system. The dispersion methods employ curved surfaces to impart rotational motions to one or more fluid flows from a pressurized container to create turbulence and improve mixing of medicament with fluid.

17 Claims, 16 Drawing Sheets

PARTICULATE DISPENSER

This application is the U.S. national phase of International Application No. PCT/GB2009/050359 filed 14 Apr. 2009, which designated the U.S. and claims priority to GB Application No. 0806735.7 filed 14 Apr. 2008, the entire contents of each of which are hereby incorporated by reference.

The present invention relates to a dispenser for a fluid, in particular a gas borne solid or liquid particulate.

Dispensers may be used to dispense particulate compositions comprising a medicament, often in metered doses into a bodily orifice, including into wounds to stimulate wound healing and in localised drug delivery with sustained-release coatings. For example during surgical operations, for spraying an anti-inflammatory or antimicrobial drug into an incision before closure. In other aspects, the dispenser may be used to dispense industrial or military particulates, e.g. as a powder fire extinguisher, such as for fire damping in electrical or electromechanical circuits.

It may also be used to dispense samples of powder and liquid products e.g. consumables, flavours and fragrances; as a spot applicator for house and garden: (a) against insect nests/infestations, (b) against plant infections, or (c) for fabric cleaning; for a wetting or lubricating action egg contact lens usage and lubrication of mechanical parts or jointed body parts (coated on hip joints for example, as alternative to full joint replacement; for protectant sprays to inhibit dissolution or erosion by adjacent fluids or devices to a protected substrate including in electronic accessories such as i-pods/mobile phones/watches; or for self-defence against an assailant e.g. for a pepper-type spay.

It may also be used to dispense adhesives in manufacturing and surgical processes/procedures egg microspheres applied to surfaces under aseptic conditions; for fluorescent or reagent application for forensic marking or reagent result enhancement; for enhancement/inhibition of bodily secretions egg in gender selection by application to semen; in assay procedures in analytical/pathology laboratories; or for applications where package contents may have to be modified to avoid allergy or toxicity egg as may be caused by certain preservatives.

A disadvantage of such devices used hitherto for solid fluid particulates is that the device often does not agitate the particulate sufficiently to ensure that substantially all of the particulate, or a consistent accurate dose of the particulate is dispensed. Another disadvantage is that the particulate may tend to clump fairly readily, especially on storage and/or in transit, with the same result. There is an increasing desire for a dispenser which avoids these disadvantages. Dispensing devices for particulates hitherto generally have failed to properly address the problem.

An object of the present invention is therefore to provide a particulate dispenser with an integral means as necessary to deaggregate and to agitate a particulate sufficiently to dispense the same as a fluid.

Another object of the present invention is to provide a device for holding particulates that are prone to clumping and for agitating the particulate with a fluid, such as a pressurised fluid, e.g. a pressurised gas, to produce a mobile fluid for safe delivery to a desired target, without exposure to the particulate, whilst ensuring that the agitation is thorough.

A further object of the present invention is to provide such a device which defines a stout enclosure around the particulate in which the particulate is protected from exposure during storage, but which is also lightweight.

Yet another object of the present invention is to provide a device which is capable of delivering an accurate dosage of a medicinal particulate which is independent of patient variation.

Another object of the present invention is to provide a device for the administration of doses of a medicament into the airways which does not rely on patient synchronisation of breathing or closing of the soft palate, or even consciousness to use.

A further object of the present invention is to provide such a device which provides a pain-free alternative to intravenous administration, and no consequent sharps hazards.

More particularly, this invention relates to a such device, and the structure of such a such device, that is adapted to provide turbulent (including cyclonic or vertical) flow agitation of particulates of widely varying shapes and sizes into a mobile fluid for delivery to a desired target.

According to a first aspect of the invention there is provided a dispenser of a fluid, in particular a gas borne solid or liquid particulate, having: a container for a fluid; a chamber for containing a particulate, in use in fluidic communication with the container; means to cause the fluid to move into the chamber from the container; means as necessary to cause the fluid to engage with particulate accommodated within the chamber to deaggregate it if aggregated and to agitate it into turbulent flow to produce a mobile fluid comprising the particulate; a discharge outlet, capable of being placed in fluidic communication with the chamber; and a release means for release of the mobile fluid from the dispenser through the discharge outlet.

When used herein the term 'turbulent flow' includes cyclonic or vortical flow, which are preferred forms of turbulent flow.

An advantage of the dispenser according to the present invention is that it may be used and will operate in any orientation. Thus it may be used in upright, inverted or laid-down fashion. Another advantage is that it solves the problem of deaggregating and/or fluidising particulates using relatively uncomplicated and potentially inexpensive technology.

The particulate is generally a solid or liquid particulate, and the present invention is particularly useful for dispensing particulate compositions comprising a medicament in metered doses, especially if the particulate is a solid particulate that tends to clump fairly readily in storage and/or in transit. The properties of any particulate may be any within a wide variety that are compatible with the function of the present device, such as its density, particle size, specific surface area, the desired dose, etc. Preferably the particles have a narrow size distribution and are of similar shape. These parameters may be conveniently controlled by appropriate selection of raw materials and/or appropriate formulation.

The fluid in the container may be any that is a sufficiently mobile fluid to agitate the particulate into turbulent flow, and is stable during storage, and is inert to the particulate and the dispensing target.

The fluid may be a gas, such as air, or if the particulate is not inert longer-term to air, nitrogen, a conventional optionally fluorinated lower hydrocarbon propellant, such as a hydroflurocarbon (HFC) or carbon dioxide; a liquid, such as water, or if the particulate is not inert longer-term to water, a (usually pressurised) conventional optionally fluorinated lower hydrocarbon propellant, such as butane or an HFC, a hydrofluoro alkane (HFA) propellant or any compatible combination thereof.

The fluid in the container should be appropriate to the intended use of the dispenser. Thus, for administration of doses of a medicament using the present dispenser, a hydrocarbon may be appropriate. When such a dispenser is used for non-medical emergency and/or accident purposes, e.g. as a powder fire extinguisher, or other like device, it will not be appropriate, and a non-flammable non-oxidant gas may be more appropriate.

Often the fluid in the container is pressurised, so that when the dispenser is used operation of the release means causes the pressurised fluid to be released into the chamber under its own pressure head.

The fluidic communication between container and chamber often comprises at least one channel, and preferably at least a pair of channels, which runs between the container and the chamber.

Any channels that run between the container and the chamber may take the form of conduits, ducts or tubes. The shape and size of any channels for agitating the particulate with the fluid may be any within a wide variety that are compatible with that function.

These may be dependent on the particular properties of the particulate, such as its density, particle size, specific surface area, the desired dose, etc, and may be of circular cross section and/or any other regular curved cross-section, e.g. a generally elliptical, semicircular or semielliptical cross-section.

However, often each will be of rectilinear cross-section, such as in the form of a slot or triangular, square or oblong cross-sectional duct.

For a quantity of a composition comprising a medicament provided in the fully laden present dispenser of 0.5-35 mg, each channel will typically have a cross-sectional area of 0.03 to 3.0 mm$^2$ and in particular 1.0 to 1.5 mm$^2$ The channels may be of widely varying shape along their length, e.g. curved, but typically are straight.

Where there is at least a pair of channels, all the channels will typically have similar and often identical dimensions and configurations. Channels in a pair of channels may of course have opposite handedness where appropriate.

Suitable examples of means to cause the fluid to move into the chamber from the container include means to reduce or sweep the internal volume of the container.

Thus, the container may be of flexible construction, supported within the dispenser of the present invention, and reduction of its internal volume may be achieved by compressing the container, e.g. with a plunger or cam acting on a wall of the container at an opposite end of the container from the chamber or at the same end as the chamber, provided that the fluid is able to move from the container to the chamber on actuation, or the container may be a generally flat tubular structure, and its internal volume may be reduced by squeezing the container towards the chamber during use with one or more rollers or wheels that are slidably mounted in the dispenser.

Alternatively, the container may be may be rigid. It may then be telescopic, i.e. it may comprise friction sliding sleeves that are gas-tight against a pressurised gas, or the structure of the container may be a cylinder that is swept by a piston.

However, the container is preferably a pressurised fluid container, such that on actuating the release means, the pressurised fluid is urged from the container into the chamber under its own head of pressure. In such cases, the release means may be the same integer as the means to cause the pressurised fluid to move into the chamber to engage with the particulate.

A pressurised fluid container has the advantage in the dispenser according to the present invention of potentially providing a more rapid and/or stronger fluid discharge into the chamber. This may be desirable to deaggregate particulate accommodated within the chamber if aggregated and to agitate it into turbulent flow to produce a mobile fluid comprising the particulate, especially if the particulate tends to clump fairly readily, on storage and/or in transit.

In one embodiment, the means to urge the particulate into turbulent flow comprises at least one channel which runs between the container and the chamber cooperating with at least one wall of the chamber, at least one baffle or deflector, or at least one other channel which runs between the container and the chamber, each of which is so configured as to urge the particulate into cyclonic, vortical or turbulent flow.

By 'cooperate' in this context is meant that flow from one integer, e.g. as fluid moves into the chamber from one or more channels that run into the latter from the container, impinges on another integer, e.g. a surface of the chamber or a baffle or deflector, and/or flow from another integer, e.g. another surface of the chamber and/or channel, and is deflected and/or reflected to cause turbulent flow in the chamber.

A preferred embodiment of the dispenser of the present invention is characterised by having at least one channel cooperating with at least one wall of the chamber.

Often, the channels for agitating the particulate with a fluid in the present dispenser are a pair of channels, running between the container and the chamber for containing the particulate, and each cooperating with a wall of the chamber.

Often the dispenser is elongate and the container and the chamber extend axially of each other. Often the fluid container and the chamber run generally along the mid-point longitudinal axis of the dispenser and are symmetrically arranged about it, as are the channels between them.

However, multiple, e.g. a pair of, channels may be configured asymmetrically about, or all on one side of the longitudinal midline of the device, e.g. to impinge on one side wall of the chamber.

In the less preferred embodiment of the dispenser of the present invention which has multiple channels not cooperating with at least one wall of the chamber to cause turbulent flow for the purpose of agitating the particulate, the channels that run between the container and the chamber may be mutually angled inwardly of the dispenser to impinge over any proportion of each other and/or to cause vortical flow about each other for agitation of the particulate.

In the preferred embodiment of the dispenser of the present invention which has a pair of channels, each cooperating with at least one wall of the chamber to cause turbulent flow for the purpose of agitating the particulate, the channels that run between the container and the chamber may be mutually angled outwardly of the dispenser at an angle of 5 to 90°, e.g. at 10 to 60° to one another.

In such an embodiment, the channels are usually configured and adapted such that the flow from them impinges on and/or (preferably) flows along at least part of a chamber wall or walls.

A more preferred embodiment of the dispenser of the present invention is characterised by a concave surface on, attached to or integral with at least part of a chamber wall or walls and so configured as to impart rotational motion to fluid and/or fluid particulate that impinges on and/or (preferably) flows along at least part of it.

Another more preferred embodiment of the dispenser of the present invention is characterised by at least two concave surfaces on, attached to or integral with at least part of a chamber wall or walls and so configured as to impart rotational motion to fluid and/or fluid particulate that impinges on and/or (preferably) flows along them from at least a pair of channels, running between the container and the chamber for containing the particulate.

Yet another most preferred embodiment of the dispenser of the present invention is characterised by at least two pairs of concave surfaces attached to or integral with at least part of a chamber wall or walls.

These are so configured as to impart rotational motion to fluid and/or fluid particulate that impinges on and/or (preferably) flows along them.

Often the dispenser is elongate and the container and the chamber extend axially of each other. Often the fluid container, the channels, and the chamber will generally be symmetrically arranged about the mid-point longitudinal axis of the dispenser.

In a most preferred embodiment, the dispenser of the present invention has at least a pair of channels, directed outwardly of the dispenser at an angle of 5 to 75°, e.g. 10 to 50°, such as at 45° to one another, the channels being configured and adapted such that the flow from each impinges on and/or (preferably) flows along at least part of a chamber wall to a concave surface on, attached to or integral with at least part of a chamber wall or walls and so configured as to impart rotational motion to fluid and/or fluid particulate that impinges on and/or (preferably) flows along at least part of it, and deflect the fluid and/or fluid particulate onto another concave surface which performs the same two functions.

In another embodiment, the dispenser of the present invention has at least one channel, the or each channel being configured and adapted such that the flow from each impinges on and/or (preferably) flows along at least part of a chamber wall to a concave surface on, attached to or integral with at least part of a chamber wall or walls and so configured as to impart rotational motion to fluid and/or fluid particulate that impinges on and/or (preferably) flows along at least part of it, and deflect the fluid and/or fluid particulate onto another concave surface which performs the same two functions.

The or each channel will often be directed outwardly of the dispenser in the same general direction. Thus, in an elongate dispenser where the container and chamber are disposed about a longitudinal midline, the or each will be at an angle to, and on the same side of the midline.

The shape and size of any concave surface for imparting rotational motion to fluid and/or fluid particulate may be any within a wide variety that are compatible with that function. These may be dependent on the particular properties of the particulate, such as its density, particle size, specific surface area, the desired dose, etc.

However, often each concave surface is of partial cylindrical cross section and/or any other regular curved surface suitable for imparting rotation to the moving fluid e.g. a generally elliptical surface.

In the preferred dispenser which is symmetrically disposed about the midline, for quantity of a composition comprising a dose of medicament provided by the present dispenser of 0.5 to 35 mg, each will typically have a radius of 0.5 mm to 3 mm—in particular 1.0 to 1.5 mm, e.g. about 1.25 mm.

Where a concave surface attached to or integral with at least part of a chamber wall or walls is configured so as to reflect the fluid and/or fluid particulate onto another concave surface, the two concave surfaces will have a respective radius of 0.5 mm to 3 mm and 0.75 mm to 4 mm and in particular 1 mm to 2 mm.

Where there is at least a first and/or second pair of concave surfaces each pair will often be of the same partial cylindrical cross section and, along with the channels, arranged symmetrically about a mid-line longitudinal axis of the dispenser. Each pair may be configured as a biconcave surface divided by a projection inwardly of and between two concave surfaces to define and section off two concave surface compartments, each to receive, impart rotation to and/or deflect and/or reflect separate fluid and/or fluid particulate flows.

A pair of channels and a first pair and optionally a second pair of such concave surfaces may be so configured as to impart contrarotational motion to fluid in the two concave surface compartments.

Such arrangements provide better agitation of the particulate than single such concave surfaces and/or channels.

With an elongate dispenser generally horizontal, the channels that run between the container and the chamber (often with the same cross-dimensions) often run in a generally horizontal direction.

Thus, optionally pressurised fluid flow from each of the channels for the purpose of agitating the particulate impinges on and/or flows along a generally vertical and generally longitudinally extending wall of the chamber. The flow may extend over any proportion, section or region of the relevant wall that is compatible with the agitating function of the dispenser.

However, the channel or channels for agitating the particulate with the optionally pressurised fluid in any embodiment of the present invention may if desired be angled upwardly or downwardly to any extent that is compatible with the agitating function of the dispenser. Again with an elongate dispenser generally horizontal, the channels may enter at or towards the top, middle or bottom of the chamber, often at or towards the base of the chamber or any concave surface compartments in the chamber.

Where the dispenser container and chamber are connected by at least two pairs of channels, corresponding (banks of) channels that run between the container and the chamber are often located in parallel alongside each other. A bank of such channels may be configured such that some of the channels run towards the top and others towards the bottom of the chamber.

The overall shape and size of the chamber may be any that is compatible with the agitating function of the dispenser. It may thus be a generally triangular, square, oblong or rhomboidal prism, or an equivalent thereof with rounded apices.

Where the chamber comprises at least two pairs of concave surfaces for agitating the particulate with the fluid, it is conveniently provided in the form of a generally triangular prism, or an equivalent thereof with rounded apices with a first pair of concave surfaces, configured as a biconcave surface divided by a projection inwardly of and between two concave surface to define and section off two concave surface compartments, at or towards one end, and a second pair of such concave surfaces also so configured at an opposing end.

For a quantity of a composition comprising a medicament provided by the present dispenser of 0.5 to 35 mg, the chamber will typically have dimensions of 0.2 to 2.5 ml.

For a dose of medicament provided by the present dispenser of 10 to 35 mg, the container will typically be capable of delivering a volume of 3 to 15 ml of propellant fluid, and in particular of 8 to 11 ml.

The chamber and any housing around it may be provided with at least one window to permit observation in the chamber that is otherwise obscured on all sides, e.g. of the agitation of the particulate, as to whether the dispenser has been used, or if it has operated satisfactorily. This may be conveniently provided in a face of the chamber lying between the first and second pairs of concave surfaces, in such an embodiment of the present invention.

The release means may take a variety of forms and/or positions, dependent on the particular properties which it is desired that the fluid particulates and/or dispenser will have. Such a release means may be provided in the form of a reversible obturating means or irreversible opening means mounted on, or integral or in communication with the channel(s) and/or the discharge outlet.

Reversible obturating means will be more suitable and advantageous for reusable and/or refillable dispensers. If alternatively, the dispensers are to be disposable, then irreversible opening means will be suitable release means.

If such means are mounted in or on a channel in the dispenser, then in general, only the container, such as a pressurised fluid container, will contain the fluid, and the chamber will not be in open fluidic communication with the discharge outlet out of use. Accordingly, in this embodiment of the present invention, the latter will need to have a temporary closure to retain the particulate in the chamber.

An advantage in a reusable and/or refillable dispenser of such means mounted in or on a channel in the dispenser is in general that they can prevent back-flow of fluid particulate into the propellant container.

Suitable release means include reversible obturating means such as reversible control devices or regulators, such as valves, including non-return valves, such as flap-valves or stopcocks, mounted on or in the channel(s) and/or the discharge outlet. These, when required, can be rotated or slid from a closed position to an open position.

Alternatively, the release means for release of the mobile fluid from the dispenser through the discharge outlet may be an irreversible opening means, mounted on or integral with the channel(s) or the discharge outlet, in use putting these integers in fluidic communication with the chamber.

Suitable examples of such means include a frangible, pierceable or cuttable bulkhead, such as a partition, panel, divider or wall that obturates the channel(s) and/or discharge outlet, with means to break, pierce and/or cut the bulkhead.

Suitable means thus include one or more (usually one) piercing points, such as a solid needle, hollow needle or quill, spike or spine. A hollow needle or quill may be provided in the present dispenser with a sharp point (so that when the bulkhead makes contact it is broken or pierced more readily). This may be in any form that can be produced by conventional hollow needle technology, e.g. produced by a straight cut across a tubular channel on a generally diagonal line, i.e. a straight bevel cut. However, the channel is preferably cut across on an arcuate generally diagonal line, to define an even sharper point at the cusp of two concave surfaces defined by the arcuate cut.

Suitable means also include one or more (usually one) sharp cutting edges, such as a straight or convex blade, e.g. a chisel, knife, lunette, and in particular a razor blade.

Any pierceable or cuttable bulkhead may be made of a relatively low-softening and/or -melting material, such as a polymeric material or relatively low $T_g$, e.g. a low-density polyethylene or a thermoplastic elastomer (TPE), such as a thermoplastic styrenic block copolymer. The means to break, pierce and/or cut the bulkhead may then be or comprise means to transfer thermal energy into the bulkhead to soften and/or melt it. Thus for example one or more (usually one) piercing points or cutting edges may be electrically heated, e.g. by induction heating.

To assist the fracture or piercing of the bulkhead, it may be provided with a zone of weakness, e.g. a thinner area, such as a depression or indentation, e.g. a dimple or notch, or an area surrounded by a thinner perimeter, such as a furrow, groove or notch, against which area the means to break, pierce and/or cut the bulkhead impinges.

Such a dispenser will be further provided with actuating means as necessary to cause the means to break, pierce and/or cut the bulkhead and the bulkhead to impinge on each other, to release the mobile fluid particulate for delivery to a desired target. Either may be fixedly mounted within the dispenser and the other is then movably mounted on or in the dispenser assembly, such that the two integers may brought into contact, e.g. with a plunger or cam acting on the moveable integer.

Where the dispenser container and chamber are connected by at least two channels, the necessary multiple release means in the channels may prove inconvenient, and it may be preferred that a single means is mounted on or in the discharge outlet.

In one embodiment, the irreversible opening means is integral with the discharge outlet, and in particular the irreversible opening means is in the form of a rigid generally hollow quill through which the discharge outlet runs, and which preferably has a rigid sharp point aligned with the (zone of weakness of the) bulkhead.

The quill is preferably fixedly mounted on the dispenser structure, e.g. often with its inner discharge outlet in register with and continuing on as a discharge outlet running to the outer surface of the dispenser.

The frangible, pierceable or cuttable bulkhead forms at least part of a wall of the chamber, which is slidably mounted in the dispenser.

In use, the chamber is urged towards the sharp point of the opening means, e.g. a quill, so that the bulkhead makes contact with and is broken or pierced by the opening means. Preferably, the bulkhead is pierced, and the chamber is pushed on further such that a seal is formed around the quill, so that loss of propellant fluid from the breach in the bulkhead around the quill is reduced. This is particularly desirable where the longitudinal extent of the orifice in the piercing means, e.g. a quill with a bevelled edge or the like exceeds the thickness of the bulkhead or its zone of weakness.

Thus, e.g. the bulkhead may be provided with a zone of weakness, such that the perimeter of the zone conforms closely to the outer surface of a hollow piercing means which impinges on and passes through the bulkhead.

Alternatively or additionally, all the bulkhead, any zone or the rest of the bulkhead around the zone may be flexible, elastically resilient and/or plastically deformable, so that it makes a seal around the hollow piercing means. Suitable materials with such properties include an elastomer blend, a thermoplastic elastomer, such as dynamically cross-linked FPDM/PP, commonly known as Santoprene, cyclic olefin polymer (COP) and cyclic olefin copolymer (COC), styrenic block copolymers such as block copolymers of styrene and butadiene or styrene, ethylene, butylene, copolymers, silicone elastomers, low-density polyethylene (LDPE) and high-density polyethylene (HDPE).

More preferably, the seal is provided and/or further enhanced by an annulus of a flexible, elastically resilient and/or plastically deformable material around the hollow piercing means, configured to abut the pierced bulkhead under slight compression at the end of the mutual travel of the bulkhead and hollow piercing means. Suitable materials for the annulus with such properties include natural and artificial rubbers and polymer materials, such as those listed above for the bulkhead or part thereof.

In such an embodiment of the present invention, the container is preferably a pressurised fluid container, such that on actuating the release means, the pressurised fluid is urged from the container into the chamber under its own head of pressure.

In such cases, the release means are the same integer as the means to cause the pressurised fluid to move into the chamber to engage with the particulate.

A pressurised fluid container has the advantage in the dispenser according to the present invention of potentially providing a more rapid and/or stronger fluid discharge into the chamber. This may be desirable to better deaggregate particulate accommodated within the chamber if aggregated and to agitate it into turbulent flow to produce a mobile fluid comprising the particulate, especially if the particulate tends to clump fairly readily, on storage and/or in transit.

The release means will be actuated by actuating means which thus indirectly cause the fluid to move into the chamber to engage with the particulate.

In the present invention, suitable examples of means for actuating the release means include for reversible obturating means: a slidable plunger or piston mounted in a wall of the dispenser, in particular an end wall of an elongate dispenser, to impart translational (in particular longitudinal) movement within the dispenser to a plunger or piston as above, or to a kink or slide valve, or rotary motion to a spigot, stopcock or other rotary valve on or in the channel(s) and/or outlet; a button which impinges on a non-return valve, or is in magnetic connection with a magnetic closure; and a cam pivotally mounted a dispenser assembly housing, acting on such a slidable plunger or piston.

Suitable example of means for actuating the release means include for irreversible opening means, a cam pivotally mounted on the dispenser and acting directly or indirectly on one of the chamber and breaking, cutting or piercing means, e.g. to impart relative (in particular longitudinal) movement within the dispenser of these two integers; a slidable plunger or piston mounted in a wall of the dispenser, in particular an end wall of an elongate dispenser, and acting directly or indirectly on one of the chamber and the breaking, cutting or piercing means to impart (in particular longitudinal) relative movement within the dispenser of these two integers.

Irreversible opening means, such as a frangible, cuttable or pierceable bulkhead that obturates the channel(s) and/or discharge outlet are of course particularly suitable for single dose dispensing of particulate compositions comprising a medicament in metered doses, or for a single use fire extinguisher, or other devices that are intended to be disposable. The irreversible opening means will then suitably be or comprise irreversible locking means to prevent re-use.

The actuating means may act directly on the release means, in the sense that, e.g. they are configured and adapted so that applying pressure to the actuating mean directly actuates the release means, e.g. causes a piercing point and a bulkhead to make contact, so that the latter is broken or pierced.

A preferred embodiment of the dispenser of the present invention is characterised by having a first part of an irreversible release means (such as breaking, cutting and/or piercing means) mounted on or integral with the discharge outlet or in the discharge outlet, together with a pressurised fluid container mounted directly on or integral with a slidable chamber having a second part of the means (such as a frangible, pierceable or cuttable bulkhead forming at least part of a wall of the chamber) which cooperates with the first part of the means in use.

Or vice versa such that the actuating means may comprise a housing which at least partly spans the chamber with at least one inwardly squeezable external wall which is pivotally mounted on a rigid support member of the housing and which actuates at least one cam, which in turn cooperates directly or indirectly in use with the chamber. Inwardly squeezing the external wall causes the or each cam to actuate the release means directly.

Alternatively, the actuating means may effectively act indirectly on the release means with the same result. For example, in the preferred embodiment of the dispenser of the present invention immediately above, an, e.g. longitudinal, actuating means may in a preferred form be configured and adapted such that in use, the second part of the means (such as a frangible, pierceable or cuttable bulkhead forming at least part of a wall of the chamber) in chamber mounted directly on or integral with a slidable fluid container is move away from the first part of an irreversible release means (such as breaking, cutting and/or piercing means) mounted on or integral with the discharge outlet or in the discharge outlet by the actuating means.

This occurs against the resistance of a kinetic energy sink until the second part is caught by a trigger which is capable of releasing energy from the energy sink.

In such an embodiment, the actuating means may comprise at least one inwardly squeezable external wall which is pivotally mounted on a rigid support member of the housing and which actuates at least one cam, which in turn cooperates directly of indirectly in use with the chamber.

Inwardly squeezing the external wall however causes the or each cam to move the two parts of the release means apart.

The energy sink may be, for example, an opposing spring bias and/or pneumatic damping bag(s). The trigger may be a spring-biased catch mechanism with a release button, so that after the container has been slid to the caught position, an inward push on the button causes the first and second parts of the release means to impact each other rapidly.

In such cases, the release means are the same integer as the means to cause the pressurised fluid to move into the chamber to engage with the particulate.

In such an embodiment of the present invention, the container is preferably a pressurised fluid container, such that on actuating the release means, the pressurised fluid is urged from the container into the chamber under its own head of pressure.

An advantage of such a dispenser according to the present invention may be that it potentially provides more rapid and efficient piercing of a bulkhead, and thus more rapid fluid flow from the container towards the chamber for the purpose of agitating the particulate more efficiently. This may be desirable to better deaggregate particulate accommodated within the chamber if aggregated and to agitate it into turbulent flow to produce a mobile fluid comprising the particulate, especially if the particulate tends to clump fairly readily, on storage and/or in transit.

Additionally, where a bulkhead makes contact with and is broken or pierced by the quill rapid movement such that the chamber is pushed on further so that the bulkhead forms a seal around the quill.

The dispenser may also be configured for the simultaneous or sequential dispensing of two different fluid materials, which must be held separately for sequential application, or for simultaneous application, e.g. because they are reactive or must be used to generate another material in situ at the point of application, or because one is a therapeutic active which is held in situ, e.g. on a surgical wound by the other, which is an adhesive and/or sustained release matrix.

In the case of, e.g. two such materials, there must be two separate vessels for two separate fluids. However, only one need be a fluid particulate in a chamber as defined herein.

If both fluids are particulates which need agitation for dispensing, then they will generally each be housed in a separate chamber with one or more channels that run between a container and the chamber, means to cause the fluid to move into the chamber from the container, a discharge outlet, capable of being placed in fluidic communication with the chamber; a release means for release of the mobile fluid from the dispenser through the discharge outlet; and actuating means for the release means.

Although separate chambers are required, any container, any outlets, any release means and any actuating means may be in common or separate, to the extent compatible with the desired simultaneous or sequential application of the materials.

In the case of simultaneous application, it will often be convenient if the release means and/or the actuating means operate in common or in parallel. In the case of sequential application, they should generally act independently.

The dispenser of the present invention may be provided with one or more use and/or tampering indicators, such as an audible signal, e.g. a click, a visual signal, e.g. a component colour change, a tactile signal, e.g. a change in component surface texture, or a tear-off seal.

It may also be provided with a locking device for security in transit and/or to prevent inadvertent actuation.

The dispenser for a fluid, in particular a gas borne solid or liquid particulate, of the present invention is particularly useful for dispensing particulate compositions comprising a medicament in metered doses, into a temporary or permanent human or other animal bodily orifice.

This includes dispensing into wounds to stimulate wound healing and in localised drug delivery with sustained-release coatings, e.g. during surgical operations, for spraying an anti-inflammatory or antimicrobial drug into an incision before closure.

Examples of such orifices include the cloaca, ear, mouth, throat and/or trachea, nostril, nasal passage, rectum, udder duct, urethra, uterus or vagina, or a lesion, such as an acute wound, e.g. a cut, gash, graze, scratch or major abrasion, a chronic wound, e.g. an abscess, sore or ulcer, or a surgical (including microsurgical) wound, e.g. an incision, ablation or lanced boil or pustule, or any device inserted in such a temporary or permanent orifice, such as a catheter, trochar, cannula, endotracheal or other endoscopic tube or an ostomy tube, e.g. a tracheostomy or colonostomy tube.

A dispenser which is configured for dispensing one or more fluid materials deep within a temporary or permanent orifice, such as the throat and/or trachea, uterus or vagina, or any device inserted in such an orifice such as a trochar, endotracheal or other endoscopic tube or an ostomy tube, e.g. a tracheostomy or colonostomy tube, may be provided with an elongate discharge outlet, capable of being placed into the orifice or device inserted in such an orifice, and generally longitudinally extending from the chamber for containing the particulate to such an extent that it is capable of delivering the discharged fluid materials, for example a quantity of a composition comprising a dose of medicament, to a desired target in the orifice, whilst the chamber for containing the particulate, the container; and the means to cause the fluid to move into the chamber from the container remain outside the orifice.

The discharge outlet generally longitudinally extending from the chamber for containing the particulate may be flexible, elastically resilient and/or plastically deformable, e.g. of materials with such properties including those known to those skilled in the art such as an elastomer blend, a thermoplastic elastomer, such as dynamically cross-linked FPDM/PP, commonly known as Santoprene, styrenic block copolymers such as block copolymers of styrene and butadiene or styrene, ethylene, butylene, copolymers, low-density polyethylene (LDPE) and high-density polyethylene (HDPE).

In such an embodiment of the present invention, the container must hold not only sufficient fluid as necessary to deaggregate and to agitate a particulate sufficiently to dispense the same as a fluid, but also to move the latter the length of the elongate discharge outlet placed into the orifice or device inserted in such an orifice.

In such an embodiment of the present invention, the container is preferably a pressurised fluid container, such that on actuating the release means, the pressurised fluid is urged from the container into the chamber under its own head of pressure.

Alternatively or additionally, all or part of the dispenser may be so configured as to be capable of being placed into the orifice or device inserted in such an orifice, and capable of delivering the discharged fluid materials, for example a quantity of a composition comprising a dose of medicament, to a desired target in the orifice, whilst the means for actuating the release means (so that the fluid is urged from the container into the chamber) remains outside the orifice.

Often the dispenser is elongate and narrow, and the container and the chamber extend axially of each other.

It will be clear to those skilled in the art that there will have to be a remote connection between the means for actuating the release means and the release means, which may be mechanical, electrical or electronic. If it is mechanical or electrical, it will generally extend longitudinally between the two means, and may have a housing around it that is flexible, elastically resilient and/or plastically deformable, as described above for the similar discharge outlet longitudinally extending from the chamber for containing the particulate.

In such an embodiment of the present invention, the container is preferably a pressurised fluid container.

In other aspects, the dispenser may be used to dispense industrial or military particulates, e.g. as a powder fire extinguisher, such as for fire damping in electrical or electromechanical circuits.

It may also be used to dispense samples of powder and liquid products e.g. consumables, flavours and fragrances; as a spot applicator for house and garden: (a) against insect nests/infestations, (b) against plant infections, or (c) for fabric cleaning; for a wetting or lubricating action e.g. contact lens usage and lubrication of mechanical parts or jointed body parts (coated on hip joints for example, as alternative to full joint replacement; for protectant sprays to inhibit dissolution or erosion by adjacent fluids or devices to a protected substrate including in electronic accessories such as i-pods, mobile phones, watches; or for self-defence against an assailant e.g. for a pepper-type spay.

It may also be used to dispense adhesives in manufacturing and surgical processes/procedures e.g. microspheres applied to surfaces under aseptic conditions; for fluorescent or reagent application for forensic marking or reagent result enhancement; for enhancement or inhibition of bodily secretions e.g. in gender selection by application to semen; in assay procedures in analytical or pathology laboratories; or for applications where package contents may have to be modified to avoid allergy or toxicity such as may be caused by certain preservatives.

A dispenser comprising a chamber and a pressurised fluid container for agitating a particulate contained in the chamber with a fluid, in accordance with this invention is described and illustrated with reference to the drawings, showing embodiments by way of example only.

BRIEF DESCRIPTION OF THE DRAWINGS

FIGS. 1*a* and 1*b* show respectively a plan view and a side view of such a dispenser.

FIGS. 2a and 2b show two longitudinal mid-line cross-sectional views, mutually at right angles, of such a dispenser.

Figure 1:
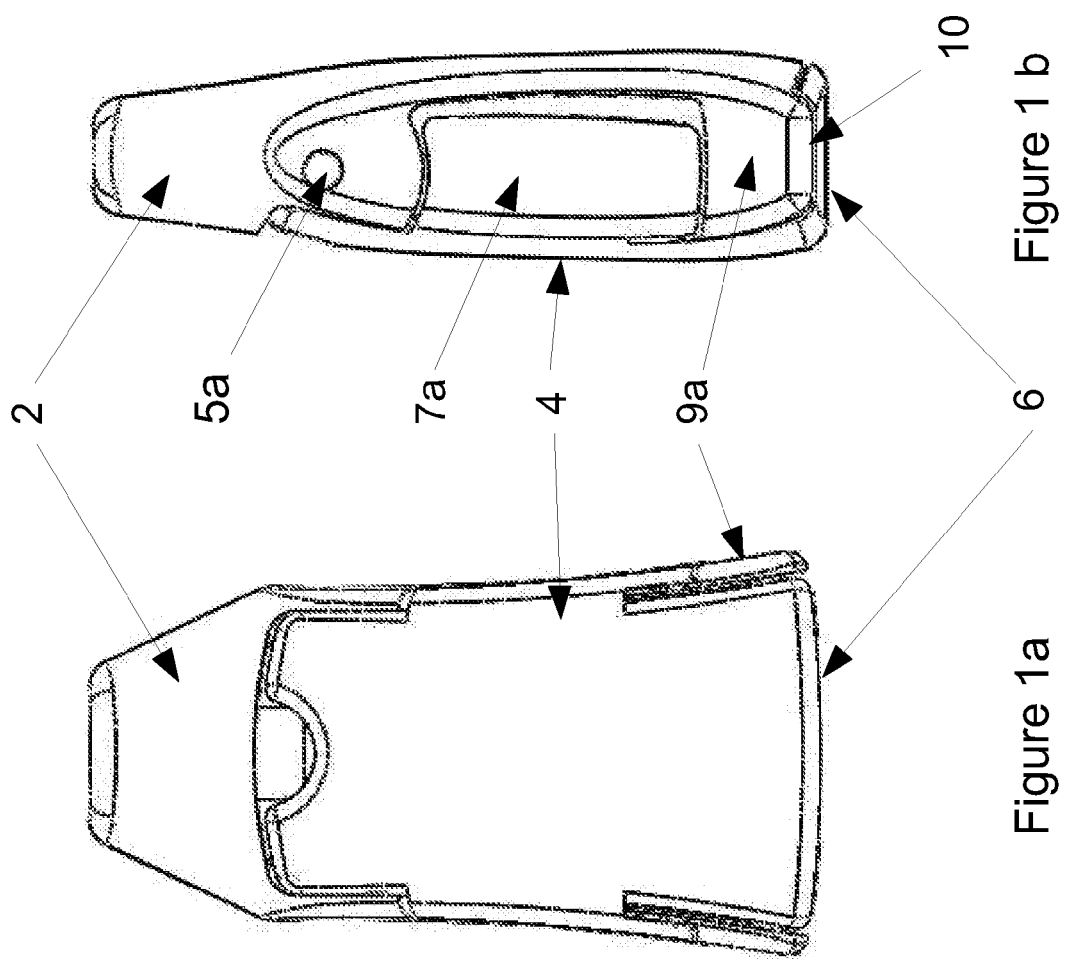
Figure 2:
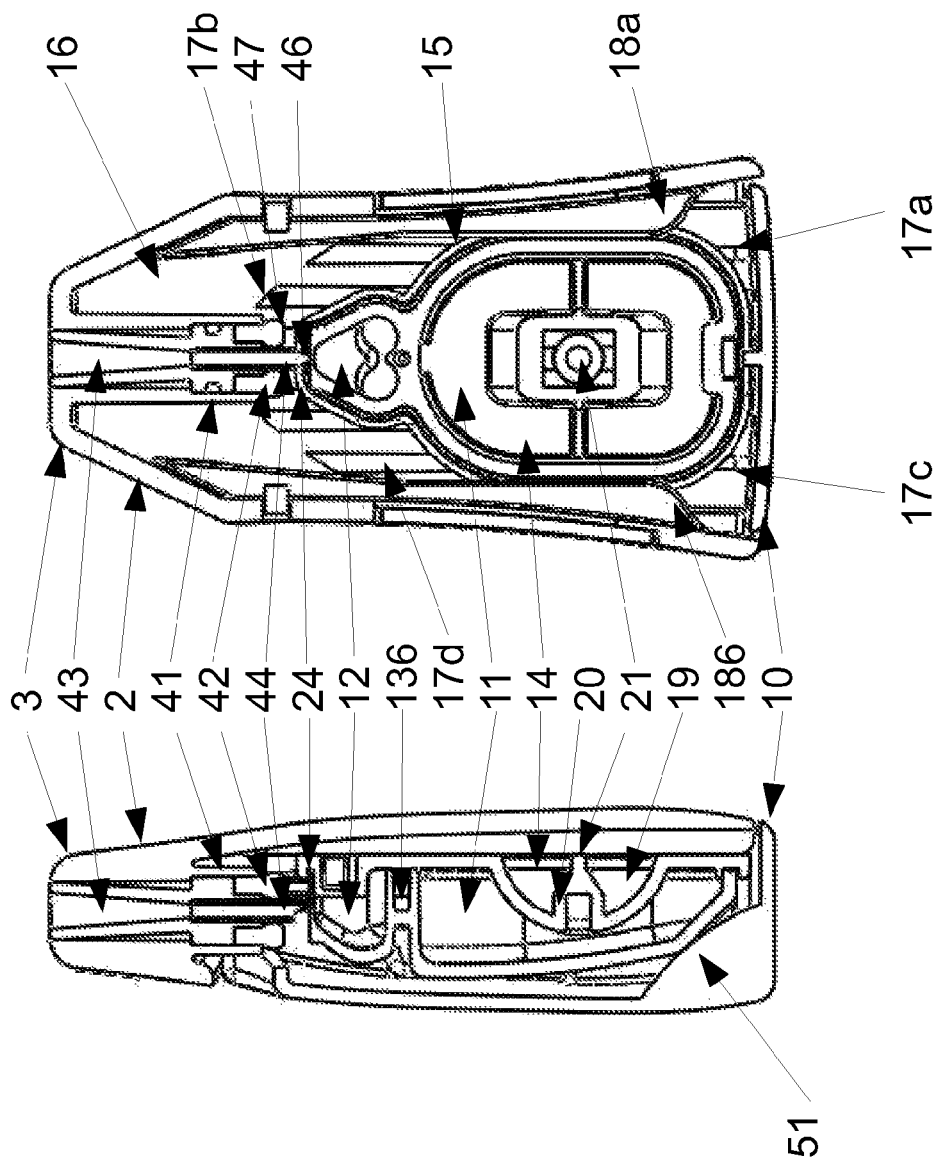

In FIGS. 1 and 2, the dispenser 1 comprises a housing 2 which encloses and is of a generally complementary shape to an assembly 3 which in turn comprises a fluid container 11 and chamber 12.

The housing 2 of the dispenser 1 has a movable cover 4 which is mounted to rotate on pivots 5a and 5b [not shown] on opposite sides of the housing 2. The housing 2 and the cover 4 are elongate in the same direction.

The cover 4 lies within the housing 2 at the pivots 5a, 5b but between there and its end 6 remote from the pivots 5a, 5b the cover 4 is provided with two side projections 7a, 7b each cooperating with a cutaway 8a, 8b in and lying flush with the housing side walls 9a, 9b. At the remote end, the cover 4 has a projection 10 extending slidably between and cooperating with the side walls 9a, 9b.

Figure 3:
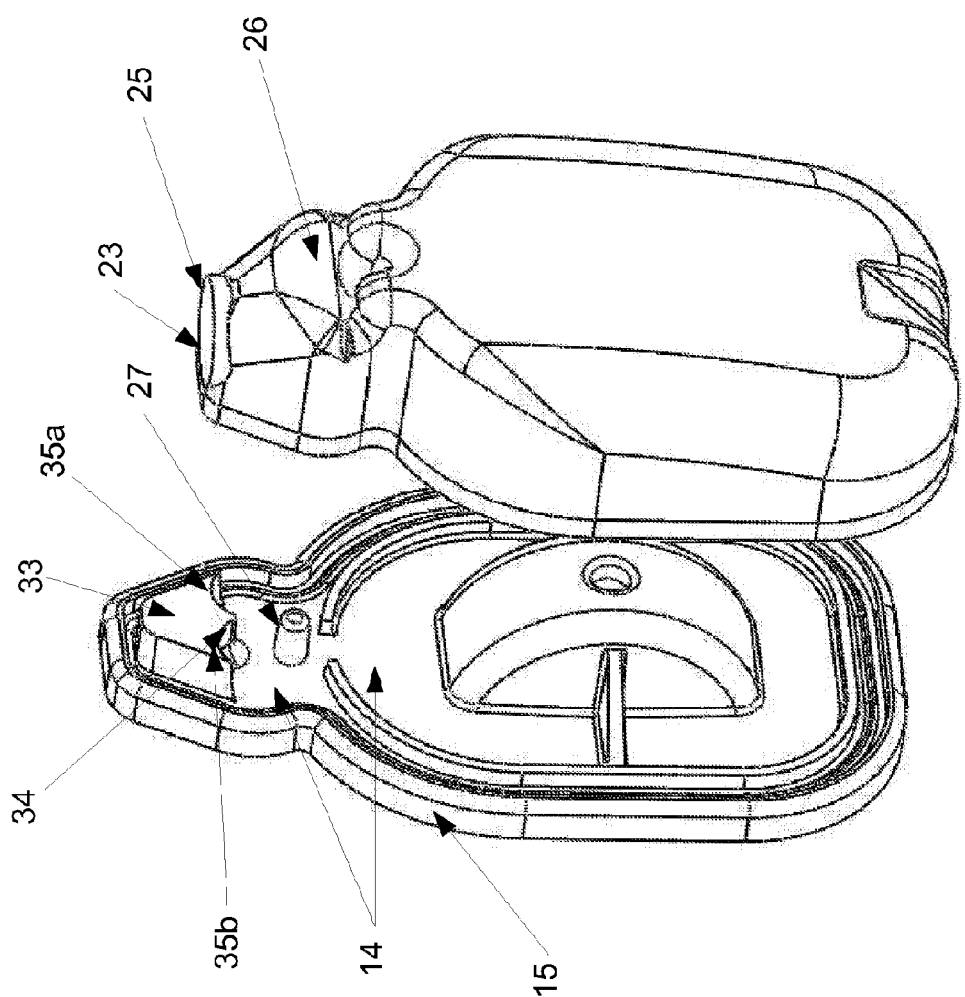
FIG. 3 shows an exploded perspective view of the assembly 3 of FIGS. 2a and 2b.
Figure 4:
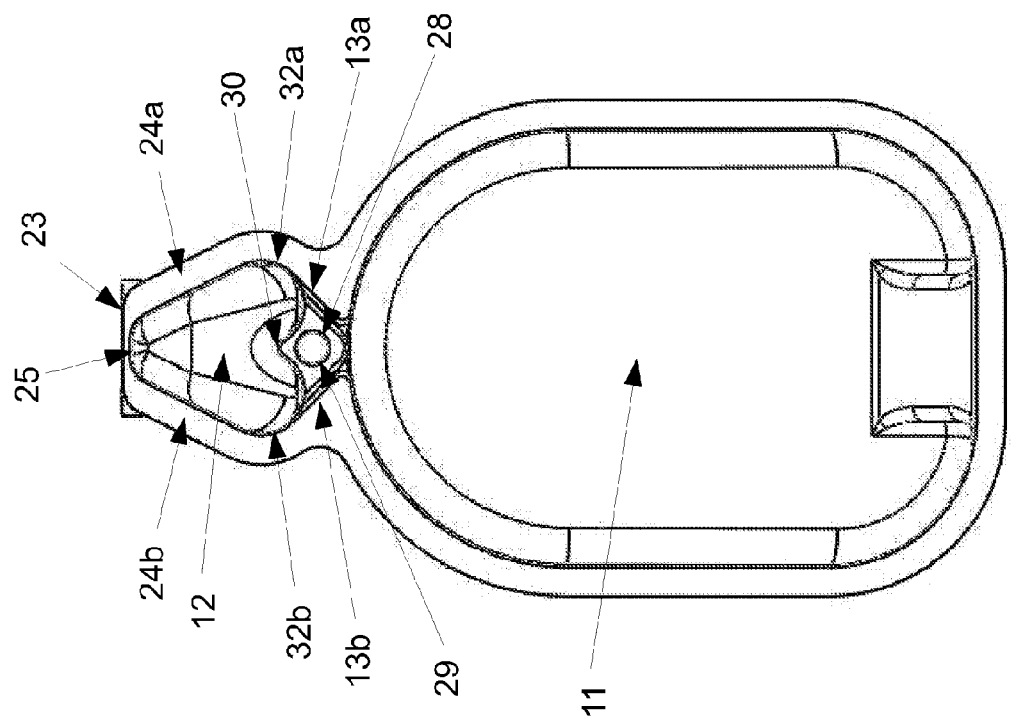
FIG. 4 shows a longitudinal view of the assembly 3 of FIGS. 2a and 2b.
Figure 5:
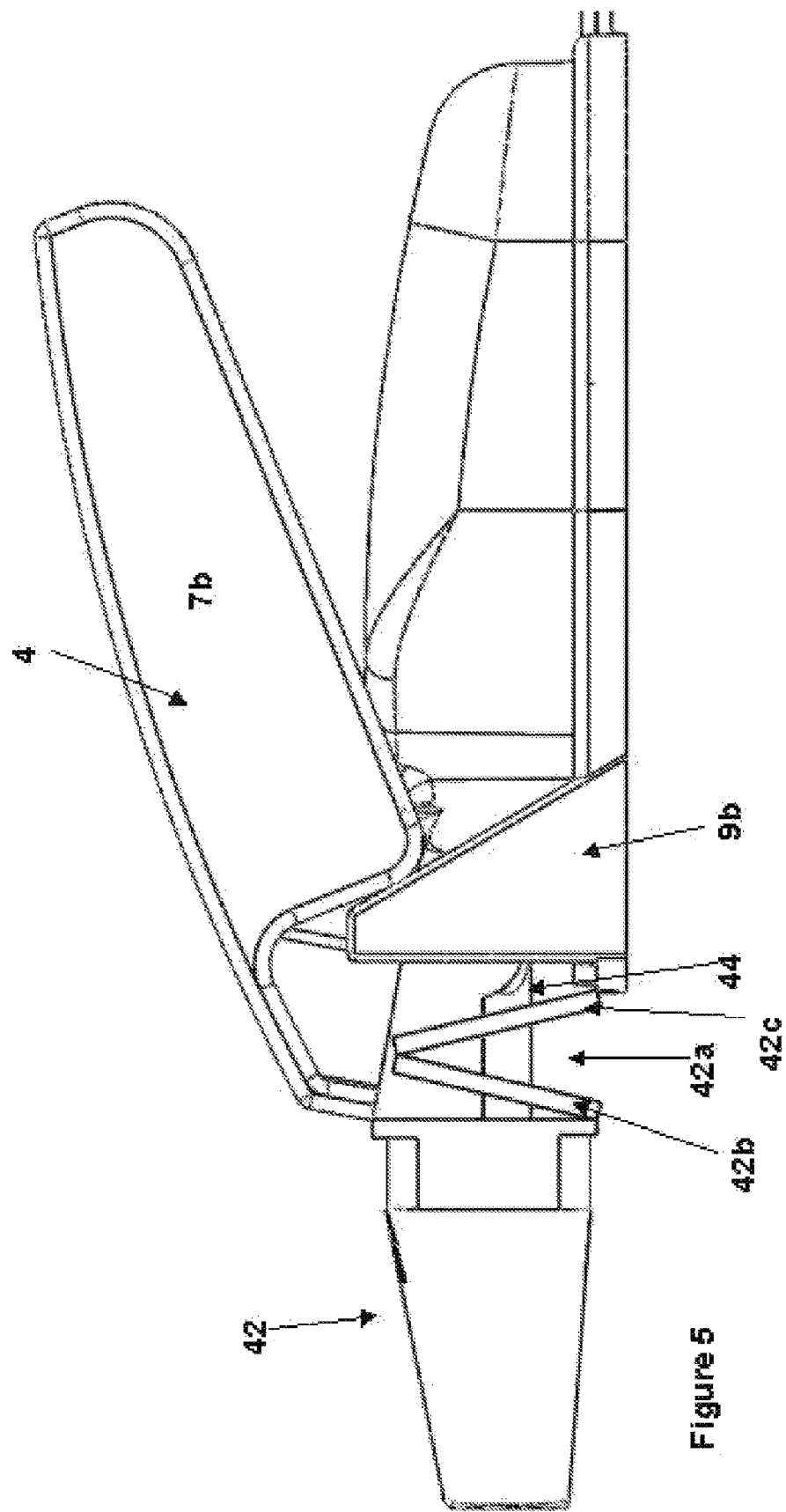
FIG. 5 shows a side view of another example of a dispenser according to the present invention.
Figure 6:
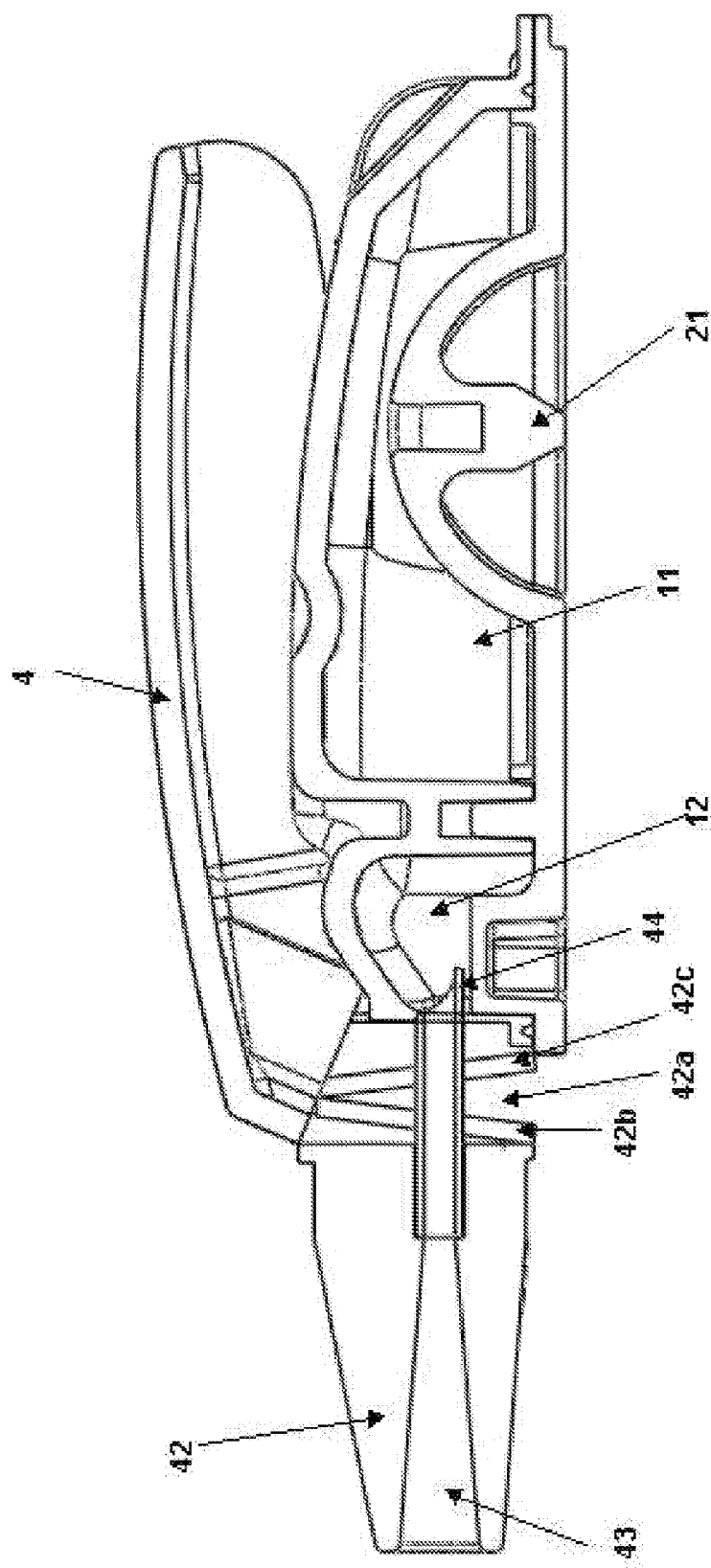
FIG. 6 shows a cross section through the example shown in FIG. 5.
Figure 7:
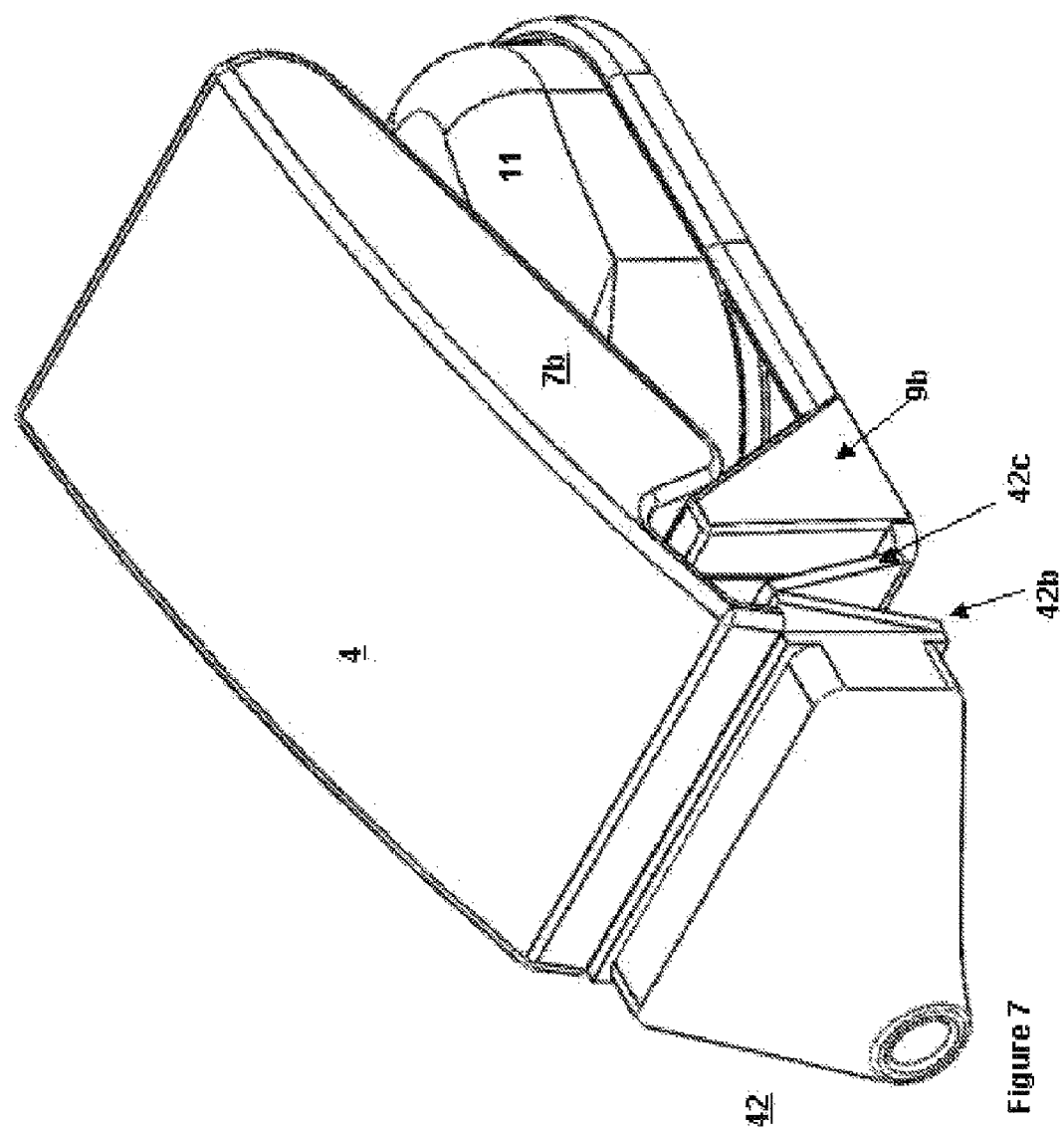
FIG. 7 shows a perspective view from above of the example shown in FIG. 5.

Referring to FIGS. 2, 3 and 4 of the drawings, an elongate dispenser 1 comprises a fluid container 11 integral with and in fluidic communication with a chamber 12 through channels 13a, 13b for containing a fluid, here pressurised gas, for agitating a solid particulate contained in the chamber 12. The container 11 and chamber 12 are arranged along and symmetrically about the mid-point longitudinal axis of the dispenser 1.

The container 11 is a generally oval vessel with a flat bottom 14 in common with the chamber 12 extending outwardly into a basal flange 15. The floor 16 of the housing is provided with four flat parallel longitudinal ribs 17a, 17b, 17c, 17d projecting inwardly of and integral with the housing floor 16 and separated by longitudinal channels.

The side walls 9a, 9b of the housing 2 are each provided with a ledge 18a, 18b projecting inwardly of the walls 9a, 9b.

The ribs 17a, 17b, 17c, 17d engage the bottom 14 of the container 11 and the ledges 18a, 18b engage the top face of the flange 15 so that the housing governs lateral and vertical movement, whilst permitting longitudinal sliding, of the container 11.

The bottom 14 of the container 11 has a hemi-cylindrical recess 19 with a central boss 20 with sealing nipple 21 rising within it. In preparation of the dispenser 1 pressurised fluid, here a gas, is pumped into the container 11 and chamber 12 to a predetermined pressure level through the then-open conduit in the boss 20) when the nipple 21 is sealed.

The chamber 12 is a hollow structure that is externally in the general form of a triangular prism, the base of which is integral with the front wall 22 of the container 11) and which is truncated by a flat front wall 23 and has two rounded apices at the angles defined by and between the two side walls 24a, 24b and the base of the triangle. Internally, the chamber 12 is generally in the form of a triangular prism with rounded apices generally of a complementary shape to the outside, so that the side walls 24a, 24b are of constant thickness.

The inner and outer surfaces of the front wall 23 of the chamber 12 however approach each other closely to form a small, relatively thin panel with a central zone of weakness 25 in its surface.

The chamber 12 has a slightly domed top 26.

A locating spigot 27 rises from the bottom 14 of the chamber 12 near its junction with the container 11. An insert 28 is located on the bottom 14 of the chamber 12 by the spigot 27 passing through a cooperating central hole 29.

The insert 28 rises the full height of the chamber 12 and is so configured as to cooperate with the side walls 24a, 24b of the chamber 12 to together define a pair of slot channels 13a, 13b.

The channels 13a, 13b are angled outwardly of the dispenser at a mutual angle of about 90° to one another, symmetrically about the mid-line longitudinal axis of the dispenser 1 and run substantially tangentially onto the concave surfaces of the interior of the chamber 12 at its rounded apices by the side walls 24a, 24b.

The insert 28 is further provided with a first upstanding integral rounded-V projection 30 to define a first biconcave surface 32a, 32b of two same partial cylindrical cross sections which runs smoothly into the rounded apical inner surfaces by the flat side walls 24a, 24b. Towards the edge where the surface 32a, 32b meets the bottom 14 of the chamber 12 it is curved perpendicularly to provide a curved skirt running into the bottom 14 of the chamber 12.

Towards the front wall 25 of the chamber 12 an integral projection 33 rises inwardly of the dispenser 1 to approximately half the depth of the chamber 12. Its outer face conforms to the inner concave surface of the interior of the chamber 12 at its rounded apex by the front wall 23.

The projection 33 is further provided with a second upstanding integral rounded-V projection 34 to define a second biconcave surface 35a, 35b of the two same partial cylindrical cross sections as the first biconcave surface 32a, 32b which runs smoothly into the rounded apical inner surfaces by the flat side walls 24a, 24b.

In a boss 41 projecting inwardly of the dispenser housing 2 a nozzle unit 42 is fixedly mounted. This unit 42 has a central duct 43 which flares towards the front end 3 of the housing 2 and has a rigid generally cylindrical hollow quill 44 fixedly mounted within its inner end 45.

The inner end 46 of the quill 44 is cut across on an arcuate generally diagonal line, to define a rigid sharp point 47 at the cusp of two concave surfaces defined by the arcuate cut.

The point 47 is aligned with the central zone of weakness 25 of the front wall 24 of the chamber 12 above the top of the projection 33.

In the angle defined by and between the inner surfaces of the cover 4 and the projection 10 lies an integral cam 51 in contact with the fluid container 11.

They are so configured that squeezing the cover 4 and housing 2 of the dispenser 1 together causes the cover 4 to rotate about the pivots 5a, 5b inwardly of the housing 2.

This in turn causes the cam 51 in contact with the fluid container 11 to urge the latter towards, and hence the chamber wall 23 onto, the sharp point 47 at the inner end 46 of the quill 44 to pierce the wall 23. Full depression of the cover 4 towards the housing 2 further urges the hollow quill through the front wall 23 of the chamber 12 such that the boss 41 seats on the front wall 23 and forms a seal around the quill 44.

When the quill 44 pierces the central zone of weakness 25 in the front wall 24 of the chamber 12, gas enters by one of two tangential channels 13a, 13b, hits smaller of two double concave surfaces 32a, 32b which are approximately half of height of double concave surfaces 34a, 34b at gas entry side. This configuration enables the quill 44 to enter above the smaller concave surfaces 32a, 32b. The gas spirals up bouncing vortically off opposite concave surfaces 35a, 35b and enlarging into the higher larger diameter area before leaving through quill 44. There is some tapering of both sets of concave surfaces 32a, 32b, 34a, 34b as evidenced by the smaller concave surfaces 32a, 32b opposite the large concave surface 35a, 35b adjacent the gas entry point. This configuration effects optimal discharge with minimal residue in the dispenser.

In this embodiment of the present invention, the container is a pressurised fluid container, so that the aperture so created releases the pressure head of fluid in the container 11 and chamber 12, causing rapid and/or strong fluid discharge into the chamber 12. Fluid flow from the channels 13a, 13b impinges on the first biconcave surface 32a, 32b and is deflected and reflected onto the second biconcave surface 34a, 34b, which in turn deflects and reflects it onto the first biconcave surface 32a, 32b. This flow produces a mobile fluid comprising the particulate in the chamber 12, even if the particulate tends to clump fairly readily, on storage and/or in transit.

Given the relative positions of the channels 13a, 13b and the duct 43, the turbulent fluid flow comprising the particulate passes over the top of the projection 35 and out through the duct 43.

Further examples of the present invention will now be described with reference to FIGS. 5 to 16. Where the features are similar or identical to the features of the example shown in FIGS. 1 to 4 like reference numerals will be used. Overall, the examples shown in FIGS. 5 to 16 operate in a similar manner to the example illustrated in FIGS. 1 to 4. As a result, only those features which differ from the example shown in FIGS. 1 to 4 will be described in detail.

FIGS. 5 to 8 illustrate a folded pouch type of dispenser 1. Unlike the example shown in FIGS. 1 to 4, the cover 4 has no projection equivalent to projection 10. The housing sidewall 9a, 9b is truncated in comparison with the housing sidewall 9a, 9b shown in FIGS. 1 to 4. The side projections 7a, 7b of the cover 4 are correspondingly more extensive so that the housing sidewall 9a, 9b and the side projections 7a, 7b of the cover between them extend to enclose the container 11 and chamber 12. The side projections 7a, 7b and the housing sidewalls 9a, 9b are tapered.

The nozzle unit 42 is augmented by the provision of a crush zone 42a or concertina that enables the quill 44 to move relative to the chamber 12. The crush zone 42a includes two elongate members 42b, 42c pivotably connected to one another and to the housing 2 and nozzle unit 42 respectively. The elongate members 42b, 42c are divided at the central axis of the housing in order to facilitate the quill 44 to extend between the members 42b, 42c.

Because the cover 4 spans to crush zone 42a and because the housing side wall 9a, 9b is tapered, when the cover 4 and the housing 2 are squeezed together the cover 4 slides along the tapered edge of the housing sidewall 9a, 9b reducing the size of the crush zone 42a and drawing the nozzle unit 42 closer to the chamber 12 thereby causing the quill 44 to impinge on and pierce the weakened wall of the chamber 12.

The provision of the crush zone provides a different mechanism for the quill to move relative to the container. As a result of the provision of the crush zone, the ribs and cam mechanism used in the example already in the patent specification are superfluous.

Figure 8:
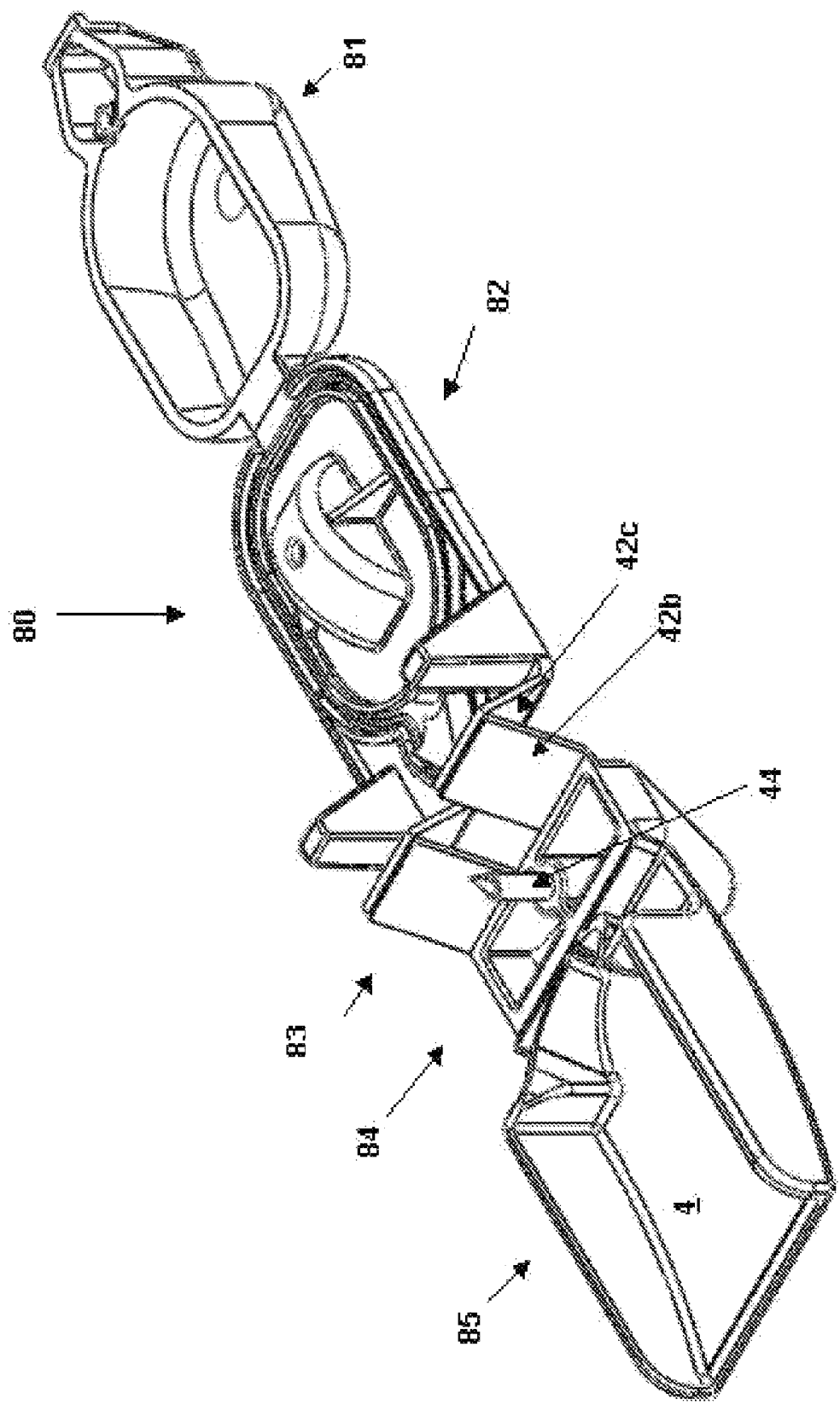
FIG. 8 shows a perspective view of a blank from which the example shown in FIG. 5 may be constructed.

The dispenser 1 is formed from a single moulded blank 80 in five zones as illustrated in FIG. 8. The first zone 81 includes the side walls and upper surface of the container 11 and chamber 12. The second zone 82 includes the flat bottom 14 of the housing 2, the integral projection 33, the hemispherical recess 19 and the sidewalls 9a, 9b. The third zone 83 consists of the crush zone 42a including two elongate members 42b, 42c. The fourth zone includes the nozzle unit 42 and the boss 41 for seating the quill 44. The fifth zone 85 includes the cover 4. All of the zones 81 to 85 are formed from a single moulded piece in a single material. The zones are pivotably connected to one another and the folds remain in tact when the dispenser 1 is complete. The blank 80 can be formed and transported in the substantially flat form and the quill 44 can subsequently be added when the dispenser is folded into shape and primed with medicament and propellant ready for use.

Figure 9:
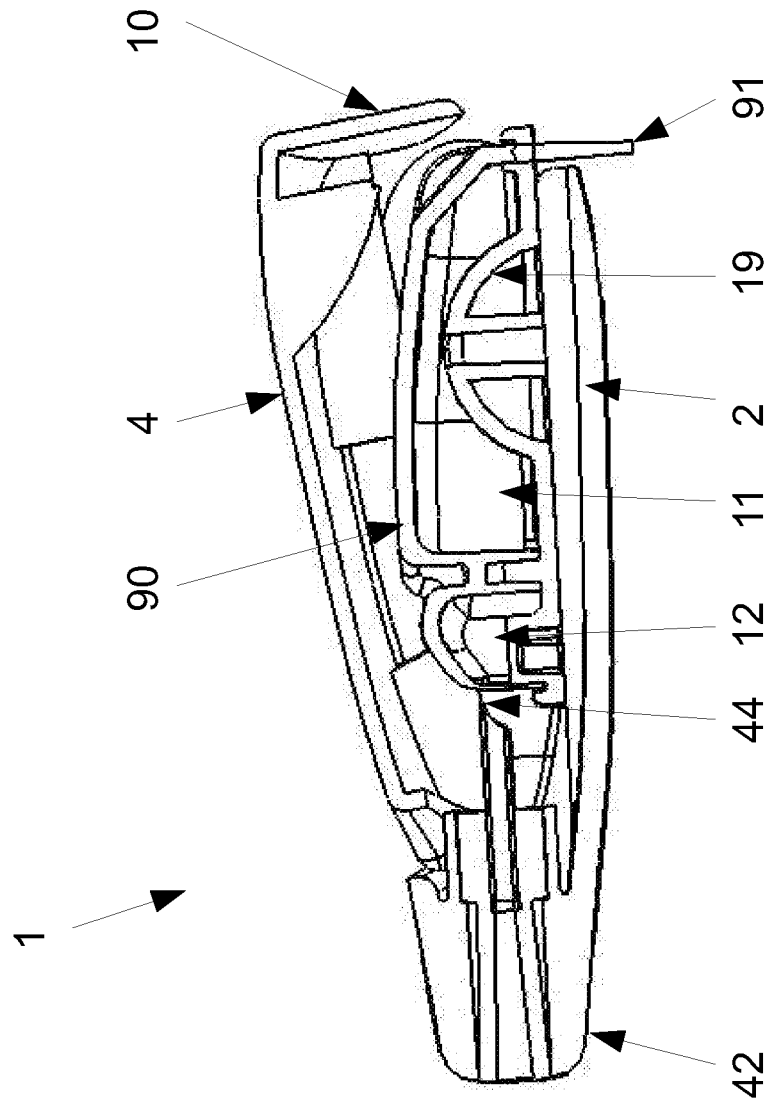
FIG. 9 shows a cross section through a further example of a dispenser according to the present invention.
Figure 10:
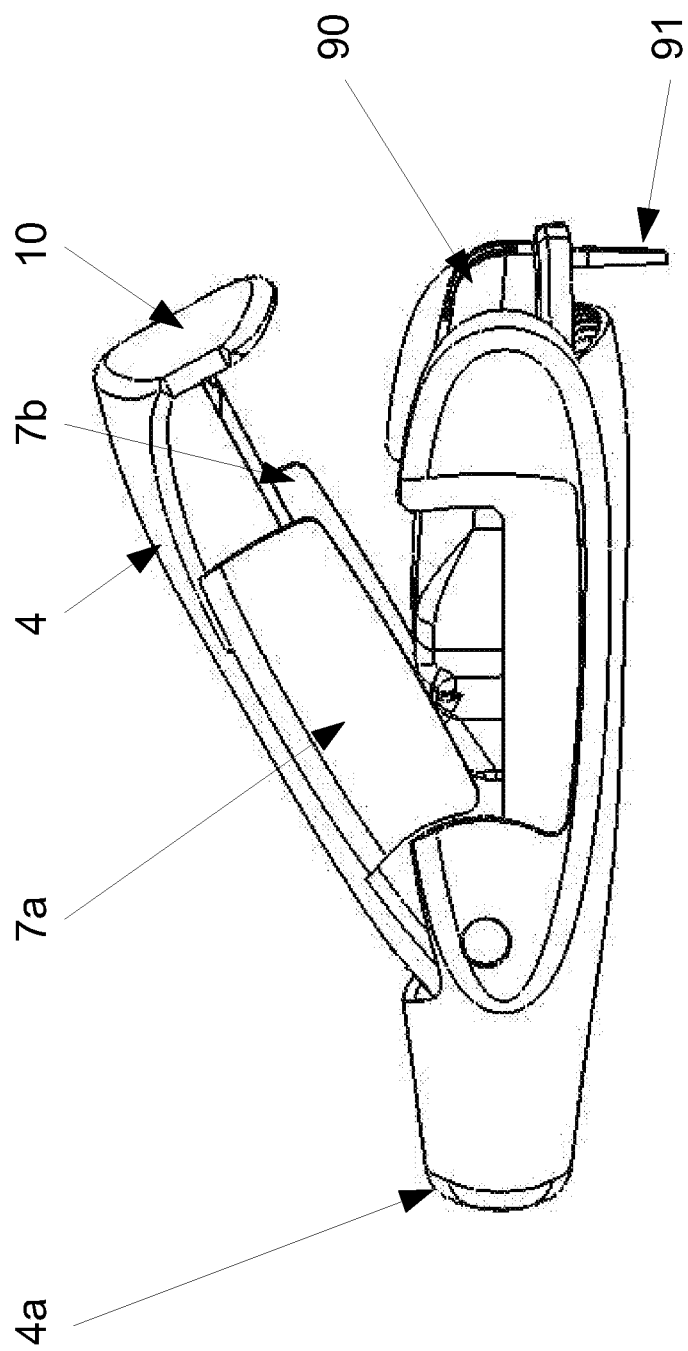
FIG. 10 shows a side view of the dispenser shown in FIG. 9.
Figure 11:
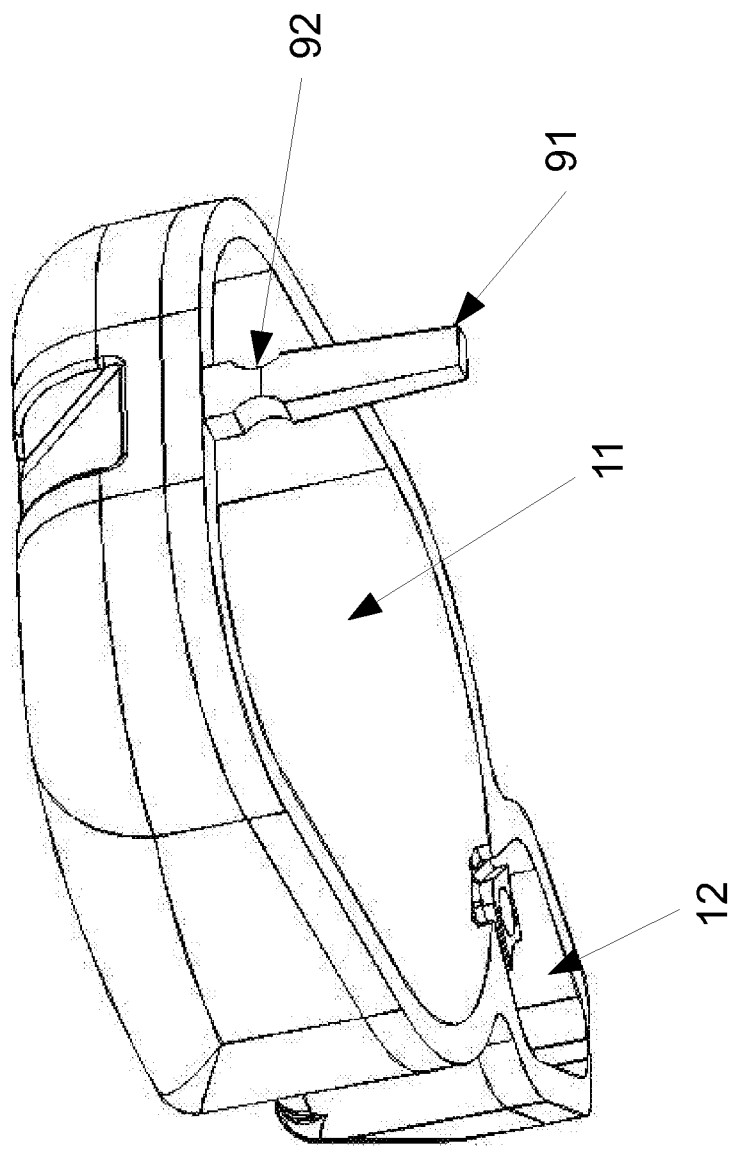
FIG. 11 shows a perspective view from beneath of a part of the dispenser shown in FIG. 9.

FIGS. 9 to 11 illustrate an example in which the container 11 and chamber 12 together form a capsule 90 that can be inserted into a housing 2. The housing 2, including nozzle unit 42 and quill 44 are therefore reused with each of a plurality of refills that are sequentially inserted into the housing 2. The actuation mechanism is substantially the same as that for the dispenser 1 illustrated in FIGS. 1 to 4 in that when the cover 4 and the housing 2 are urged together, the cam 51 moves the capsule 90 along the guide rails 17 until the weakened wall of the container 11 comes into contact with the quill 44.

A tab 91 is provided on the capsule 90 that protrudes beyond the housing 2 in the vicinity of the projection 10 at the back of the cover 4. The provision of this tab 91 impedes the movement of the capsule 90 into the housing 2 and thereby prevents inadvertent actuation of the dispenser 1. The tab 91 is shown most clearly in FIG. 11. The tab 91 extends from the face of the container 11 that is adjacent to the projection 10 from the cover 4, in use. The tab 91 is elongate and has a frangible portion 92 which may consist of a narrowing or one or more perforations. The frangible portion 92 enables the tab 91 to be torn off when the dispenser 1 is prepared for use. The provision of the tab 91 ensures that the dispenser 1 cannot be accidentally actuated.

Figure 12:
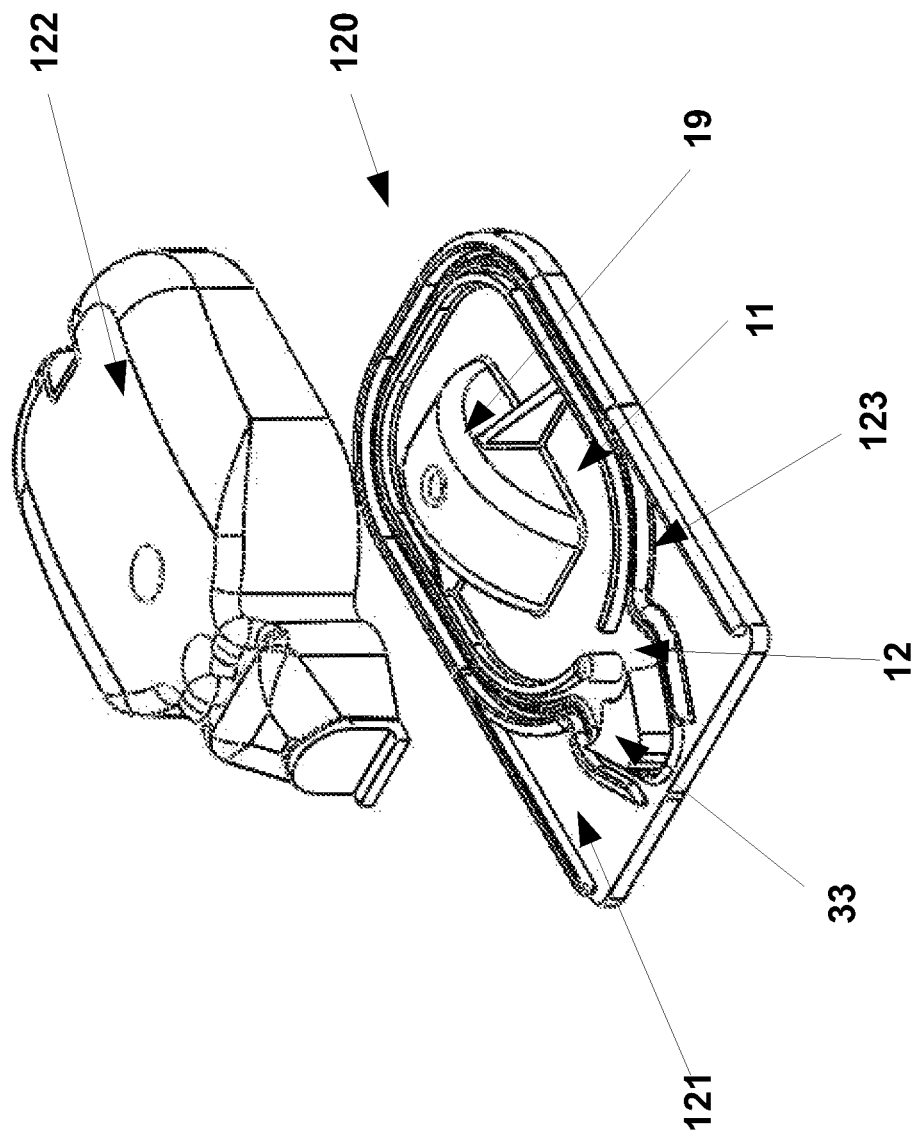
FIG. 12 shows an exploded view of an alternative cartridge for use in any one of the dispenser shown in the preceding figures.
Figure 13:
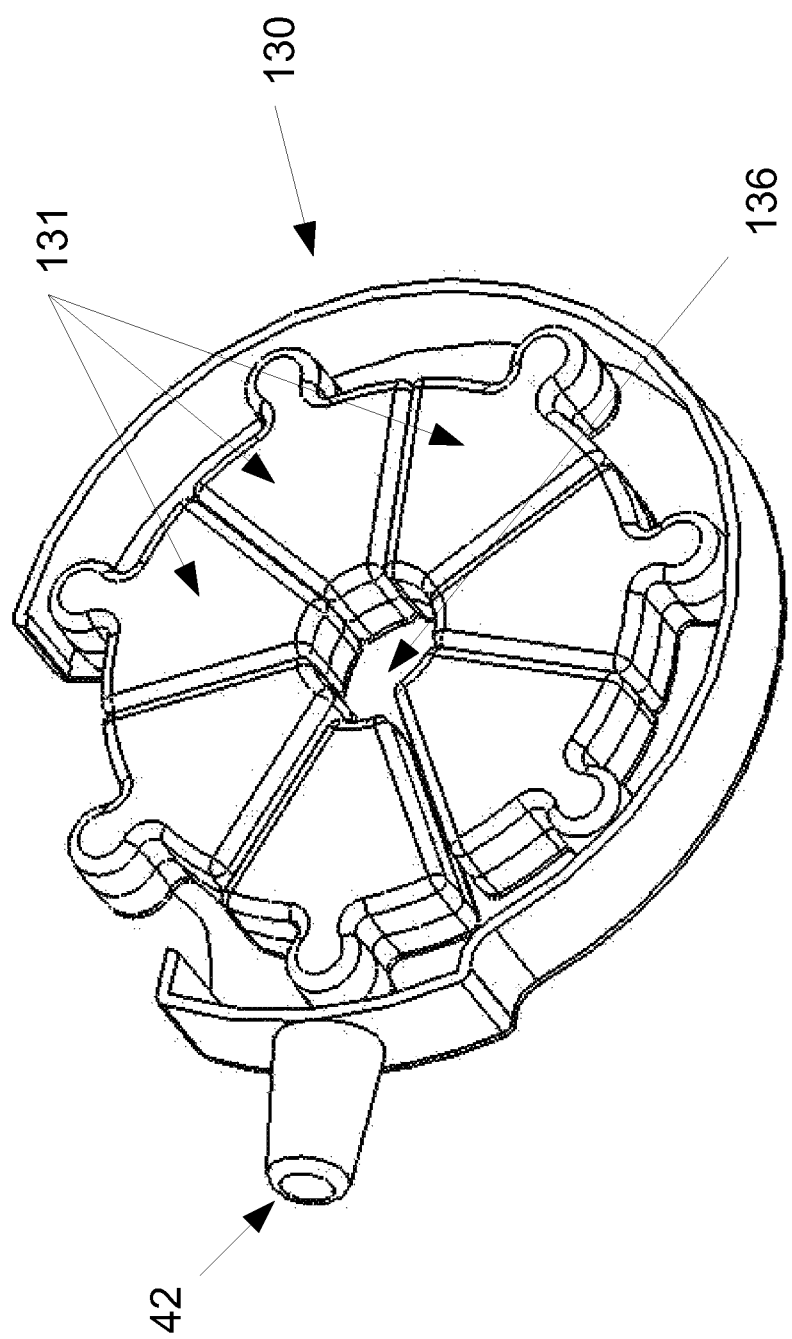
FIG. 13 shows a cut away view of a further example of a dispenser according to the present invention.
Figure 14:
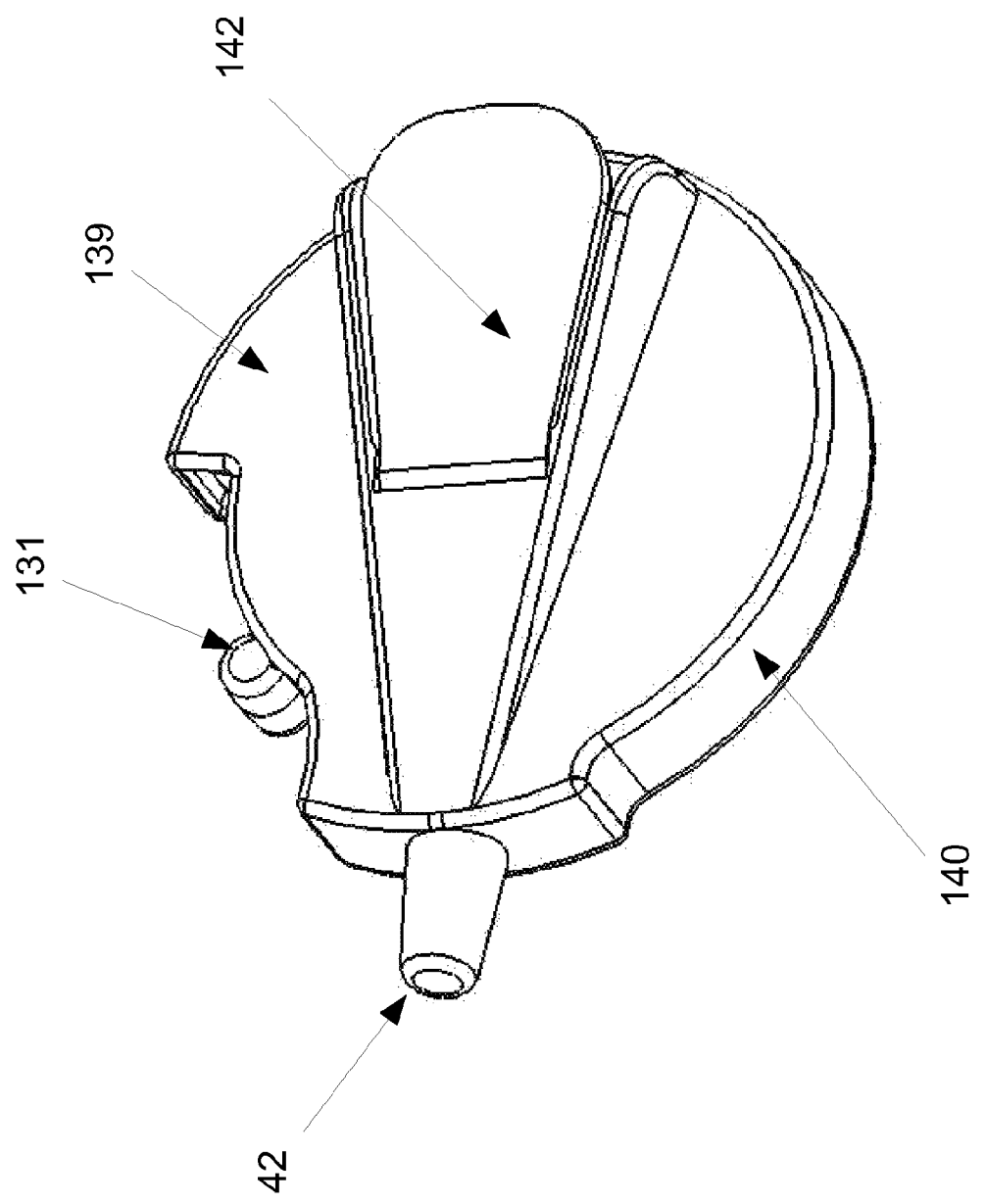
FIG. 14 shows a perspective view from above of the dispenser shown in FIG. 13.
Figure 15:
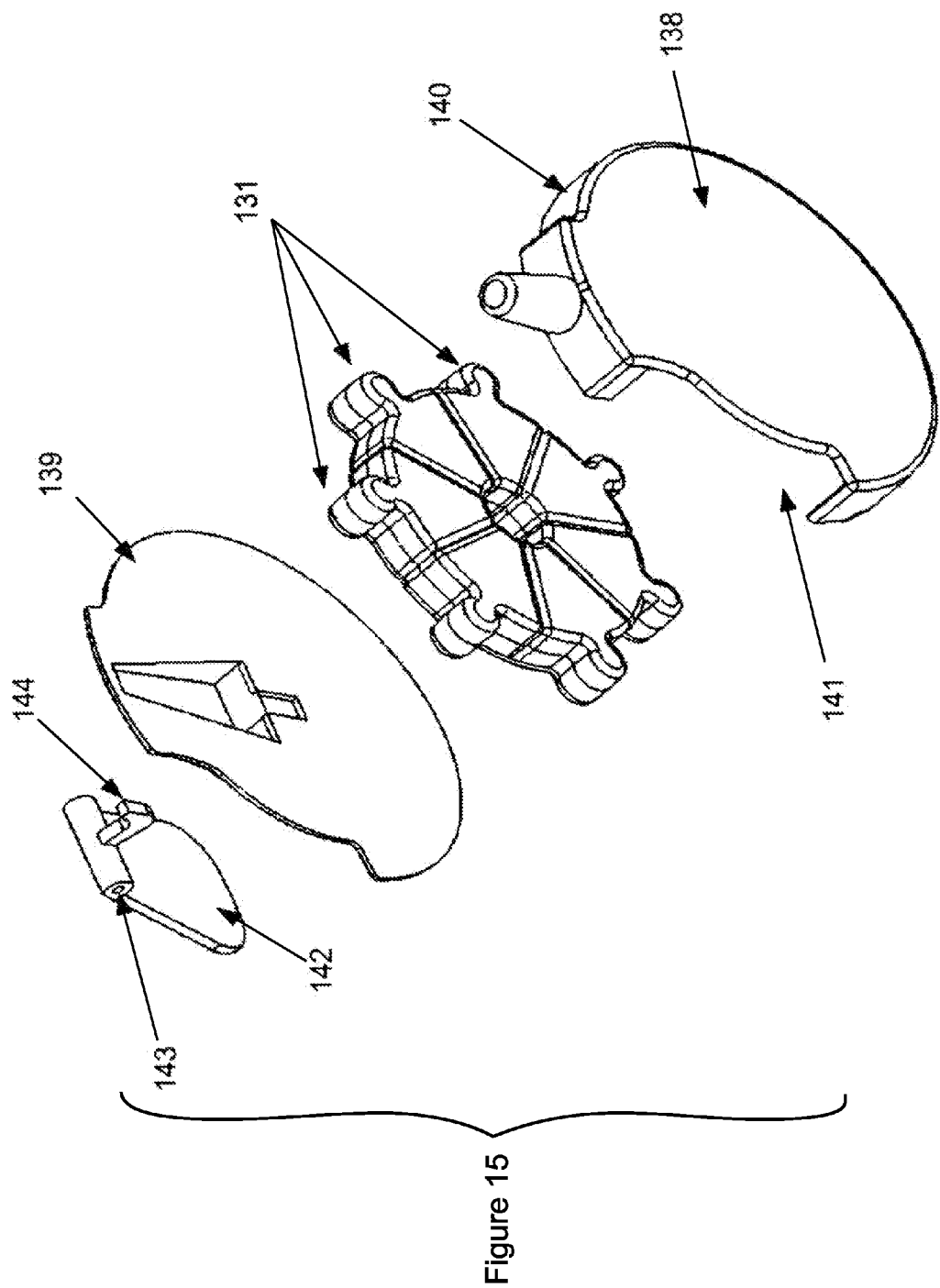
FIG. 15 shows an exploded diagram of the constituent parts of the dispenser shown in FIG. 13.
Figure 16:
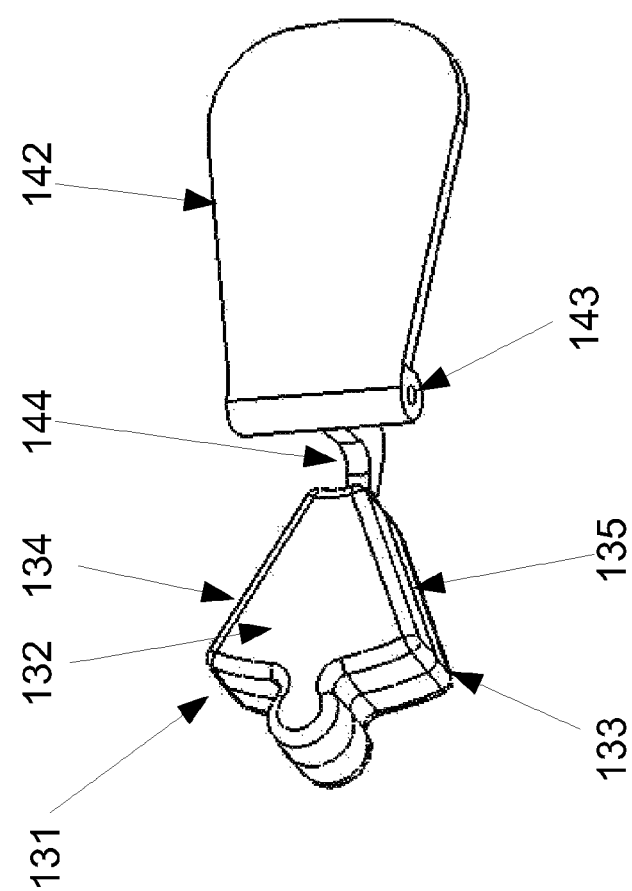
FIG. 16 shows part of the actuation mechanism employed in the dispenser shown in FIG. 13.

FIG. 12 shows an alternative capsule 120 that can be used in the dispenser 1 illustrated in FIGS. 1 to 4 or 9 to 11. The capsule 120 has an extended base 121 and a cap 122. The shape of the base 121 closely conforms to the sidewalls and end portion of the container 11 furthest distant from the chamber 12. The base 121 then extends beyond the shoulder 123 of the container 11 up to a point parallel to the weakened end wall of the chamber 12. The cap 122 has an envelope that closely conforms to the outer profile of the container 11 and chamber 12. The provision of an extended base 121 makes the capsule 120 more robust as it is less likely to flex at the point where the container 11 and the chamber 12 meet. The more robust form ensures, therefore, that the weakened end wall of the chamber is correctly positioned to be pierced by the quill 44 in use.

FIGS. 13 to 16 illustrate a circular dispenser configured to dispense a plurality of doses. The dispenser takes the form of a pouch 130 that is configured to hold seven capsules or wedges 131 each of which comprises a container 11 and a chamber 12. Each wedge 131 has a substantially flat top 132 and a substantially flat base 133 and side walls 134, 135 that extend orthogonally between the top 132 and the base 133. Each wedge 131 is an equal segment of a circle which is truncated in order to provide a small central area 136 about which the wedges 131 are mounted to enable them to be rotated within the pouch 130.

The pouch 130 takes the form of a slim circular disc comprising a circular base 138, a circular top 139 and an annular side wall 140. Part of the side wall is cut away so that the outer wall of the chamber of one of the wedges 131 is available to the user through the gap 141 in the pouch. The user can therefore rotate the wedges 131 using a cam system (not shown) so that a different wedge 131 is adjacent the nozzle unit 42.

The circular top 139 is provided with a flap 142. The flap 142 is pivotably mounted on the circular top 139 so that it can move between a position substantially flush with the circular top 139 and a position in which the part of the flap furthest distant from the pivot protrudes above the circular top 139. The flap 142 is provided, at a position beyond the pivot point 143, with a hook 144. The hook 144 is configured to bear against the wedge 131 that is aligned for actuation. When the flap 142 is pivoted so that it becomes flush with the circular top 139, the hook 144 urges the wedge 131 into position for actuation.

There are seven wedges 131, one for use on each day of the week. However, for different dosage regimens, different numbers of wedges 131 could be used, for example 3, 4, 5, 6, 8, 9 or 10 wedges 131.

In a further alternative, not illustrated in the drawings, the wedges are mounted on a carousel which is rotated on guide rails that interface with the side walls of one of the wedges to ensure that wedge is correctly positioned for actuation. The wedges are mounted on a carousel which is a circular platen with radial ridges between which the wedges can be secured. The ridges may extend over part or substantially all of the radius of the carousel, but do not extend into the central area. The carousel is rotatably mounted on the base of the pouch so that it can rotate relative to the pouch.

The provision of a number of wedges within a single pouch does not increase the overall size of the pouch considerably in comparison with a system with a single container because only one nozzle unit, one quill and one actuation mechanism is required. The pouch has a diameter in the region of 50 mm to 100 mm, preferably 60 mm and each of the wedges can contain a payload of 1 to 30 mg including medicament together with suitable excipients.

Although all of the dispensers 1 shown in the accompanying drawings have a single nozzle unit with a single central duct, a further example is envisaged that comprises two of any one of the illustrated examples, formed back to back to provide two nozzle unit spaced apart such that each nozzle can discharge medicament into one nostril. The provision of a pair of dispensers in a back to back configuration enables actuation of the two devices simultaneously by compressing the two covers towards one another by pinching them between finger and thumb, for example. In this way, medicament can be simultaneously dispensed into both nostrils by a single actuation action. The two dispensers could be prepared separately and then joined, or alternatively they may be formed together with a common base.

The invention claimed is:

1. A capsule for use in a dispenser for a medicament, the capsule comprising a pressurised container for a fluid, a chamber for containing a particulate, at least one channel running between the container and the chamber to provide fluidic communication between the container and chamber in use, and at least two distinct concave surfaces on or integral with at least part of an internal wall or internal walls of the chamber, the concave surfaces so arranged that once fluidic communication between the chamber and container is established to create a fluid flow from the container to the chamber through the at least one channel and toward the concave surfaces, each concave surface imparts a rotational motion to a fluid flow or portion of fluid flow that impinges upon it, so that within the chamber a rotationally turbulent flow of fluid is produced in order to engage with the particulate and to produce a mobile fluid comprising the particulate.

2. The capsule of claim 1, in which the rotational motion imparted to the fluid flow or portion thereof is cyclonic or vortical.

3. The capsule of claim 1 wherein there are two distinct concave surfaces and each imparts a rotational motion to a fluid flow or portion of fluid flow that is contrarotational to the rotational motion imparted by the other.

4. The capsule of claim 1 wherein the fluid in the container is a gas.

5. The capsule of claim 1 having one or more of the at least one channels cooperating with the internal wall or at least one of the internal walls of the chamber.

6. The capsule of claim 1 wherein the chamber comprises two portions of at least partially cylindrical cross-section, each portion comprising one of said concave surfaces.

7. The capsule of claim 1 wherein the chamber comprises two conjoined side by side substantially cylindrical portions each comprising one of said concave surfaces.

8. The capsule of claim 7 wherein the at least one channel comprises one channel that introduces fluid tangentially into at least one of the substantially cylindrical portions.

9. The capsule of claim 7 wherein the at least one channel comprises two channels, wherein each of the channels introduces fluid tangentially into a respective cylindrical portion.

10. The capsule of claim 1 further comprising release means comprising a frangible, piercable or cuttable wall of the capsule.

11. A dispenser comprising a capsule according to claim 1.

12. The dispenser according to claim 11 wherein the capsule is integrated with the dispenser.

13. The dispenser according to claim 11 wherein the dispenser is configured to accommodate more than one capsule.

14. The dispenser according to claim 13 wherein a plurality of capsules are arranged in a circular array and wherein each capsule is shaped as a circular segment.

15. A dispenser comprising a capsule according to claim 10 further comprising a discharge outlet capable of being placed in fluidic communication with the chamber of the capsule via the frangible, piercable or cuttable wall.

16. The dispenser according to claim 15 further comprising a means of breaking, piercing or cutting the frangible, piercable or cuttable wall so as to place the chamber in fluidic communication with the discharge outlet.

17. The dispenser of claim 16 wherein the means for breaking, piercing or cutting is a hollow quill for piercing the frangible, piercable or cuttable wall of the chamber to enable the mobile fluid to exit the capsule and the dispenser via the discharge outlet.

* * * * *